United States Patent
Chen et al.

(10) Patent No.: US 9,977,028 B2
(45) Date of Patent: May 22, 2018

(54) IONIZATION OF CHEMICALS IN MIXTURE AT LOW PH BY AMBIENT IONIZATION/MASS SPECTROMETRY

(71) Applicant: Ohio University, Athens, OH (US)

(72) Inventors: Hao Chen, Athens, OH (US); Ning Pan, Jinan (CN); Pengyuan Liu, Dandong (CN)

(73) Assignee: Ohio University, Athens, OH (US)

( * ) Notice: Subject to any disclaimer, the term of this patent is extended or adjusted under 35 U.S.C. 154(b) by 176 days.

(21) Appl. No.: 14/441,385

(22) PCT Filed: Nov. 7, 2013

(86) PCT No.: PCT/US2013/068925
§ 371 (c)(1),
(2) Date: May 7, 2015

(87) PCT Pub. No.: WO2014/074701
PCT Pub. Date: May 15, 2014

(65) Prior Publication Data
US 2015/0293116 A1    Oct. 15, 2015

Related U.S. Application Data

(60) Provisional application No. 61/723,473, filed on Nov. 7, 2012.

(51) Int. Cl.
*G01N 33/68* (2006.01)
*H01J 49/16* (2006.01)
(Continued)

(52) U.S. Cl.
CPC ....... *G01N 33/6848* (2013.01); *C12Q 1/6806* (2013.01); *G01N 33/66* (2013.01);
(Continued)

(58) Field of Classification Search
None
See application file for complete search history.

(56) References Cited

U.S. PATENT DOCUMENTS

2003/0106797 A1* 6/2003 Schneider ........ G01N 27/44726
204/452
2004/0079881 A1    4/2004 Fischer et al.
(Continued)

FOREIGN PATENT DOCUMENTS

EP    2051283 A2    4/2009

OTHER PUBLICATIONS

Hartmanova et al., "Fast profiling of anthocyanins in wine by desorption nano-electrospray ionization mass spectrometry" Journal of Chromatography A, vol. 1217, Issue 25, Jun. 18, 2010.*
(Continued)

*Primary Examiner* — Wyatt Stoffa
*Assistant Examiner* — James Choi
(74) *Attorney, Agent, or Firm* — Wood Herron & Evans LLP

(57) ABSTRACT

A mass spectrometry-based method for analyzing an acidic organic target compound includes directing a charged solvent (44) toward a pre-acidified sample (12) comprising the target compound, to thereby ionize the pre-acidified sample (12). The method further includes directing the ionized pre-acidified sample (54) to a mass spectrometer (18), the mass spectrometer (18) being configured to identify and quantify the target compound.

13 Claims, 18 Drawing Sheets

(51) Int. Cl.
*G01N 33/66* (2006.01)
*C12Q 1/68* (2018.01)
*H01J 49/00* (2006.01)

(52) U.S. Cl.
CPC ...... *G01N 33/6842* (2013.01); *H01J 49/0031* (2013.01); *H01J 49/165* (2013.01)

(56) References Cited

U.S. PATENT DOCUMENTS

| | | | |
|---|---|---|---|
| 2007/0228271 A1 | 10/2007 | Truche et al. | |
| 2007/0259410 A1 | 11/2007 | Donaldson et al. | |
| 2008/0087811 A1* | 4/2008 | Knapp | H01J 49/0463 250/282 |
| 2008/0314129 A1 | 12/2008 | Schultz et al. | |
| 2009/0095900 A1 | 4/2009 | Whitehouse et al. | |
| 2010/0059674 A1 | 3/2010 | Chen et al. | |
| 2010/0258717 A1 | 10/2010 | Chen et al. | |
| 2011/0253903 A1 | 10/2011 | Sun et al. | |
| 2012/0286155 A1 | 11/2012 | Mulligan | |
| 2013/0023005 A1 | 1/2013 | Chen et al. | |

OTHER PUBLICATIONS

Samalikova et al., "Interpreting conformational effects in protein nano-ESI-MS spectra" Anal Bioanal Chem (2004) 378.*
Ficarro et al., "Phosphoproteome analysis by mass spectrometry and its application to *Saccharomyces cerevisiae*" Nature Biotechnology 20, (2002).*
Konermann et al., "Unfolding of Proteins Monitored by Electrospray Ionization Mass Spectrometry: A Comparison of Positive and Negative Ion Modes" J Am Soc Mass Spectrom 1998, 9, 1248-1254.*
Kharlamova et al., "Electrospray Droplet Exposure to Gaseous Acids for the Manipulation of Protein Charge State Distributions", Anal. Chem. 2010, 82, 7422-7429.*
Bai, H.; Ho, S. W. Polym. Int. 2011, 60, 26-41.
Bond, A. M.; Colton, R.; D'Agostino, A.; Downard, A. J.; Traeger, J. C. Anal. Chem. 1995, 67, 1691-1695.
Childers, C. L.; Huang, H.; Korzeniewski, C. Langmuir 1999, 15, 786-789.
D.R., P.; L.M., R. Polymer 2008, 49, 3187-3204.
Djilali, N. Energy 2007, 32, 269-280.
International Preliminary Report on Patentability in International Patent Application No. PCT/US2013/063048, dated Jan. 19, 2016, 6 pgs.
International Preliminary Report on Patentability in International Patent Application No. PCT/US2013/068922, dated May 12, 2015, 10 pgs.
International Search Report and Written Opinion in International Patent Application No. PCT/US2013/063048, dated May 3, 2014, 8 pgs.
International Search Report and Written Opinion in International Patent Application No. PCT/US2013/068922, dated Feb. 11, 2014, 14 pgs.
Iwasita-Vielstich, T. Advances in Electrochemical Science and Engineering; VCH Verlagsgesellschaft: Weinheim: Germany, 1990.
Jusys, Z.; Massong, H.; Baltruschat, H. J. Electrochem. Soc. 1999, 146, 1093-1098.
Leuthold, L. A.; Mandscheff, J. F.; Fathi, M.; Giroud, C.; Augsburger, M.; Varesio, E.; Hopfgartner, G. Rapid Commun. Mass Spectrom. 2006, 20, 103-110.
Ota, K. I.; Nakagawa, Y.; Takahashi, M. J. Electroanal. Chem. 1984, 179, 179-186.
Permentier, H. P.; Bruins, A. P. J. Am. Soc. Mass Spectrom. 2004, 15, 1707-1716.
Permentier, H. P.; Jurva, U.; Barroso, B.; Bruins, A. P. Rapid Commun. Mass Spectrom. 2003, 17, 1585-1592.
Roussel, C.; Dayon, L; Lion, N.; Rohner, T. C.; Josserand, J.; Rossier, J. S.; Jensen, H.; Girault, H.H. J. Am. Soc. Mass Spectrom. 2004, 15, 1767-1779.
Song, C. Catal Today 2002, 77, 17-49.
Steele, B. C. H.; Heinze!, A. Nature 2001, 414, 345-352.
Sun, X.; Miao, Z.; Yuan, Z.; Harrington, P. B.; Colla, J.; Chen, H. Int. J. Mass Spectrom. 2011, 301, 102-108.
Thiam, H. S.; Daud, W. R. W.; Kamarudin, S. K.; Mohammad, A. B.; Kadhuma, A. A. H.; Loh, K. S.; Majlan, E. H. Int. J Hydrogen Energy 2011, 36, 3187-3205.
Wang, H.; Rus, E; Abruna, H. D. Anal. Chem. 2010, 82, 4319-4324.
Wasmus, S. et al., "Real-Time Mass Spectrometric Investigation of the Methanol Oxidation in a Direct Methanol Fuel Cell", Journal of the Electrochemical Society, vol. 142, No. 11, Nov. 1995, pp. 3825-3833.
Wolter, O.; Heitbaum, J. Ber. Bunsen-Ges. Phys. Chem. 1984, 88, 2-6.
Xu, X.; Lu, W.; Cole, R. B. Anal. Chem. 1996, 68, 4244-4253.
Zhang, Y.; Chen, H. Int. J. Mass Spectrom 2010, 289, 98-107.
Zhao, W. et al., "Complete Quantitative Online Analysis of Methanol Electrooxidation Products via Electron Impact and Electrospray Ionization Mass Spectrometry", Analytical Chemistry, vol. 84, No. 13, Jul. 3, 2012, pp. 5479-5483.
Zhao, W. et al., "Quantitative Online Analysis of Liquid-Phase Products of Methanol Oxidation in Aqueous Sulfuric Acid Solutions Using Electrospray Ionization Mass Spectrometry", Analytical Chemistry, vol. 82, No. 6, Mar. 15, 2010, pp. 2472-2479.
Zhao, W. et al., "Quantitative Online Detection of Volatile and Non-volatile Methanol Electrooxidation Products by Combined Electron Impact Mass Spectrometry and Electrospray Ionization Mass Spectrometry", ECS Transactions, vol. 35(12), 2011, pp. 9-19.
Zhou, F.; Van Berkel, G. J. Anal. Chem. 1995, 67, 3643-3649.
Aebersold, R. et al., Chem. Rev. 2001, 101, 269-296.
Becker, J.S. et al., Int. J. Mass Spectrom. 2003, 228, 985-997.
Bogialli, S. et al., "Confirmatory analysis of sulfonamide antibacterials in bovine liver and kidney: extraction with hot water and liquid chromatography coupled to a single- or triple-quadrupole mass spectrometer", Rapid Communications in Mass Spectrometry, vol. 17, No. 11, Jun. 15, 2003, pp. 1146-1156.
Chowdhury, S.K. et al., J. Am. Soc. Mass Spectrom. 1990, 1, 382-388.
Chrisman, P.A. et al., J. Am. Soc. Mass Spectrom. 2005, 16, 1020-1030.
Denes, J. et al., Anal. Chem. 2009, 81, 1669-1675.
Dixon, R.B. et al., J. Am. Soc. Mass Spectrom. 2007, 18, 1844-1847.
Fenn, J.B. et al. Science 1989, 246, 64-71.
Ferguson, C.N. et al., Anal. Chem. 2011, 83, 6468-6473.
Gronborg, M. et al., Mol. Cell Proteomics 2002, 1, 517-527.
Hartmanova, L. et al., "Fast profiling of anthocyanins in wine by desorption nano-electrospray ionization mass spectrometry", Journal of Chromatography A, vol. 1217, No. 25, Jun. 1, 2010, pp. 4223-4228.
Hu, L. et al., Angew. Chem. 2011, 123, 4219-4222; Angew. Chem. Int. Ed. 2011, 50, 4133-4136.
Hunter, T., Cell 2000, 100, 113-127.
International Preliminary Report on Patentability in corresponding International Patent Application No. PCT/US2013/068925, dated May 12, 2015, 8 pgs.
International Search Report and Wirritten Opinion in corresponding International Patent Application No. PCT/US2013/068925, dated Mar. 13, 2014, 11 pgs.
Kharlamova, A. et al., J. Am. Soc. Mass Spectrom. 2011, 23, 88-101.
Krasny, L. et al., "In-situ enrichment of phosphopeptides on MALDI plates modified by ambient ion landing", Journal of Mass Spectrometry, vol. 47, No. 10, Oct. 27, 2012, pp. 1294-1302.
Kweon, H.K. et al., Anal. Chem. 2006, 78, 1743-1749.
Lane, A. et al., Proc. Natl. Acad. Sci. USA 2009, 106, 7314-7319.
Li, J. et al., Anal. Chem. 2009, 81, 9716-9722.
Lu, M. et al., Anal. Bioanal. Chem. 2012, 403, 355-365.
Ma, X. et al., Anal. Chem. 2008, 80, 6131-6136.

(56) References Cited

OTHER PUBLICATIONS

McLachlin, D.T. et al., Curr. Opin. Chem. Biol. 2001, 5, 591-602.
Miao, Z. et al., Anal. Chem. 2011, 83, 3994-3997.
Miao, Z. et al., J. Am. Soc. Mass Spectrom. 2009, 20, 10-19.
Miao, Z. et al., J. Am. Soc. Mass Spectrom. 2010, 21, 1730-1736.
Pan, N. et al., "Highly efficient ionization of phosphopeptides at low pH by desorption electrospray ionization mass spectrometry", The Analyst, vol. 138, No. 5, Jan. 1, 2013, p. 1321.
Perry, R.H. et al., Angew. Chem. 2011, 123, 264-268; Angew. Chem. Int. Ed. 2011, 50, 250-254.
Porath, J. et al., Nature 1975, 258, 598-599.
Posewitz, M.C. et al., Anal. Chem. 1999, 71, 2883-2892.
Poulter, L. et al., Biochim. Biophys. Acta 1987, 929, 296-301.
Qiu, B. et al., "Desorption electrospray ionization mass spectrometry of DNA nucleobases: implications for a liquid film model", Journal of Mass Spectrometry, vol. 44, No. 5, May 1, 2009, pp. 772-779.
Salih, E., Mass Spec. Rev. 2005, 24, 828-846.
Takats, Z. et al., Science 2004, 306, 471-473.
Takats, Z. et al., Anal. Chem. 2004, 76, 4050-4058.
Vasicek, L. et al., Anal. Chem. 2009, 81, 7876-7884.
Venter, A.R. et al., Anal. Chem. 2010, 82, 1674-1679.
Wiseman, J.M. et al., Chem. 2005, 117, 7127-7130; Angew. Chem. Int. Ed. 2005, 44, 7094-7097.
Xie, Y. et al., J. Am. Chem. Soc. 2006, 128, 14432-14433.
Zhang, Y. et al., Anal. Chem. 2012, 84, 3838-3842.
Zhang, Y. et al., Chem. Comm. 2011, 47, 4171-4173.
Zhang, Y. et al., J. Proteome Res. 2011, 10, 1293-1304.
Zubarev, R.A. et al., J. Am. Chem. Soc. 1998, 120, 3265-3266.
Office Action in U.S. Appl. No. 14/441,245 dated Jun. 14, 2016, 9 pgs.
U.S. Patent and Trademark Office, Office Action in U.S. Appl. No. 14/441,245, dated Sep. 7, 2016, 9 pgs.

* cited by examiner

RPKHPIKHQGLPQEVLNENLLRFFVAPFPEVFGKEKVNELSKDIG$_p$SE$_p$STEDQAMEDIKQMEAE$_p$SI$_p$S$_p$S$_p$SEEIV
PN$_p$SVEQKHIQKEDVPSERYLGYLEQLLRLKKYKVPQLEIVPN$_p$SAEERLHSMKEGIHAQQKEPMGIVNQELA
YFYPELFRQFYQLDAYPSGAWYYVPLGTQYTDAPSFSDIPNPIGSENSEKTTMPLW (SEQ. ID. NO.10)

FIG. 3A

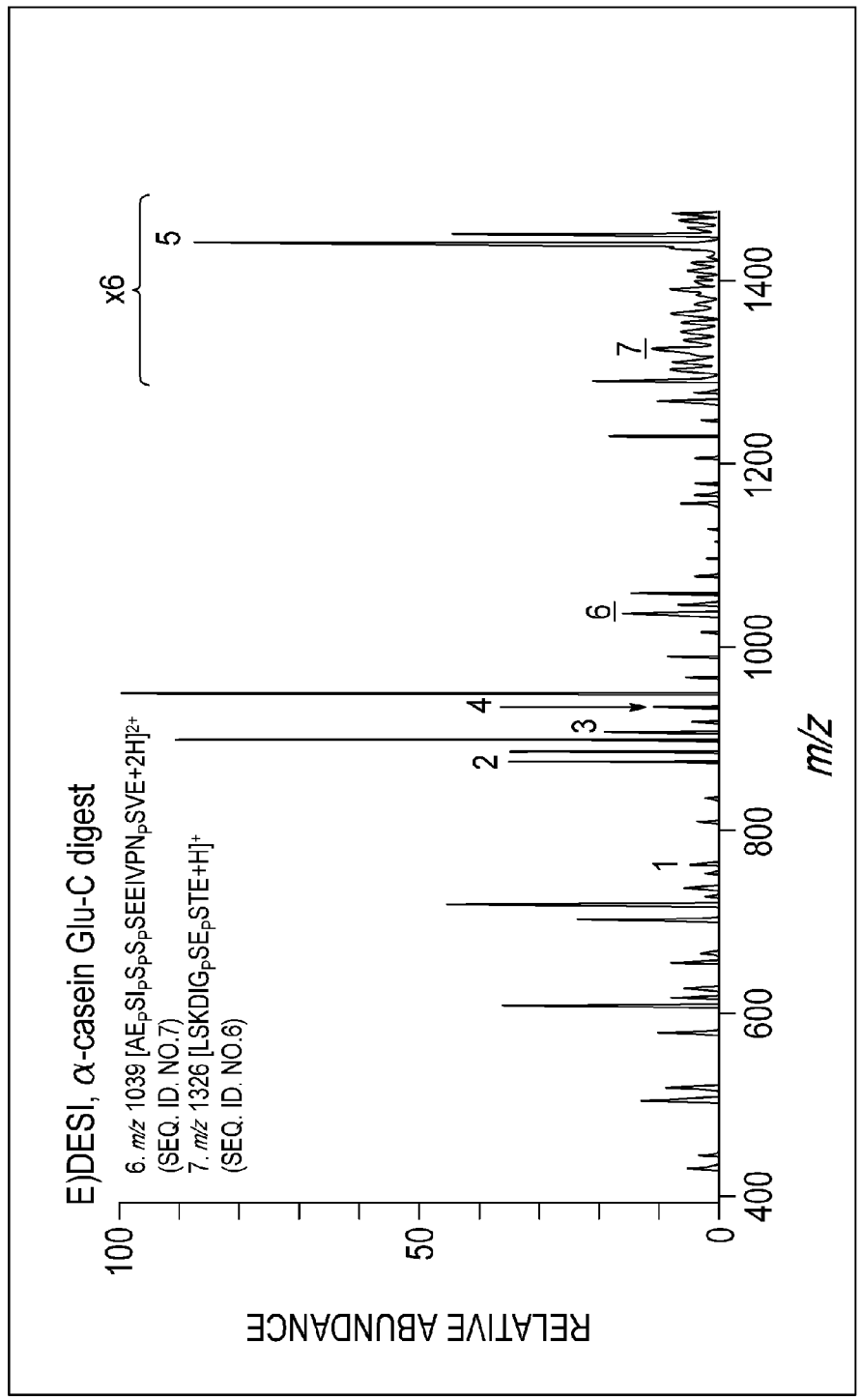

RELEELNVPGEIVE$_P$SL$_P$S$_P$S$_P$SEESITRINKKIEKFQ$_P$SEEQQQTEDELQDK
IHPFAQTQSLVYPFPGPIPNSLPQNIPPLTQTPVVVPPFLQPEVMGVSKV
KEAMAPKHKEMPFPKVPVEPFTESQSLTLTDVENLHLPLLQSWMH
QPHQPLPPTVMFPPPQSVLSLSQSKVLPVPQKAVPYPQRDMPIQAFLLYQ
EPVLGPVRGPFPIIV(SEQ. ID. NO.26)

IONIZATION OF CHEMICALS IN MIXTURE AT LOW PH BY AMBIENT IONIZATION/MASS SPECTROMETRY

CROSS-REFERENCE TO RELATED APPLICATION

This application claims the benefit of U.S. Provisional Patent Application Ser. No. 61/723,473, filed on Nov. 7, 2012, the disclosure of which is incorporated herein by reference in its entirety.

STATEMENT REGARDING FEDERALLY SPONSORED RESEARCH

This invention was made with government support under CHE0911160 awarded by the National Science Foundation. The government has certain rights in the invention.

TECHNICAL FIELD

The present invention is generally related to a method for ionization of chemicals in a mixture. In particular, the present invention is related to ionization of phosphopeptides in mixtures by ambient ionization/mass spectrometry.

BACKGROUND

Phosphorylation is one of the most common post-translational modifications (PTM) of proteins (approximately 30% of cellular proteins are phosphorylated), and it plays an important role in a wide range of biological processes, such as signal transduction. Phosphorylation is the addition of a phosphate ($PO_4^{3-}$) group to a protein or other organic molecule. Phosphorylation turns many protein enzymes on and off, thereby altering their function and activity. Protein phosphorylation in particular plays a significant role in a wide range of cellular processes. Its prominent role in biochemistry is the subject of a very large body of research.

Mass spectrometry (MS) has become an increasingly viable technology for phosphoprotein analysis. However, a major challenge in this regard is that phosphopeptide signal in the positive ion mode is severely suppressed by non-phosphorylated peptides when a phosphoprotein digest is ionized by traditional ionization methods such as electrospray ionization (ESI) in a commonly used "bottom-up" approach. Preliminary purification of phosphopeptides prior to MS analysis is often indispensable to solve the problem, using antibodies, affinity chromatography, metal oxides, nanopolymers, or nanoparticles to enrich phosphopeptides. As separation and purification could be time-consuming, a direct, rapid and sensitive method for ionizing phosphopeptides in mixtures would be instrumental to facilitating their analysis and characterization.

Desorption electrospray ionization (DESI) is a recent advance in the field of MS. DESI provides direct ionization of analytes with little or no sample preparation. Sample ionization by DESI occurs via the interactions with charged microdroplets generated in a pneumatically assisted electrospray of an appropriate solvent. In addition to analysis of solid samples, DESI has been extended to directly ionize liquid samples, and its demonstrated applications include the coupling MS with chromatography, microfluidics, and electrochemistry, probing protein conformation, and developing submilli-second time-resolved MS.

SUMMARY

The present invention is premised on the realization that an organic compound can be analyzed at low pH (i.e., in strong acidic media) using a mass spectrometer at very low pH by DESI. DESI utilizes a regular solvent as an ionizing electrospray, which, in turn, directs analyte compound to a mass spectrometer configured to analyze the analyte. Potential damage to the mass spectrometer caused by strong acid in sample mixture can be prevented due to the use of regular spray solvent, which is neutral or slightly acidic and can dilute the sample during the DESI ionization process.

The present invention is further premised on the realization that phosphoproteins can be successfully analyzed utilizing DESI coupled with MS. More particularly, the phosphopeptide can be acidified with a strong acid, such as hydrochloric acid, which suppresses the deprotonization of the peptide phosphate groups in solution. The acidified phosphopeptide can then be ionized using DESI, whereby the ionizing electrospray effectively dilutes the acidified phosphopeptide, allowing it to be analyzed using MS without damaging the mass spectrometer.

The objects and advantages of the present invention will be further appreciated in light of the following detailed description and drawings provided herein.

BRIEF DESCRIPTION OF THE DRAWINGS

The accompanying drawings, which are incorporated in and constitute a part of this specification, illustrate embodiments of the invention and, together with a general description of the invention given above and the detailed description given below, serve to explain the principles of the invention.

FIG. 3A is an α-casein sequence according to Experiment 2.

FIGS. 3B-3E are α-casein digests according to Experiment 2.

FIG. 6A is a β-casein sequence according to Experiment 5.

DETAILED DESCRIPTION

Figure 1:
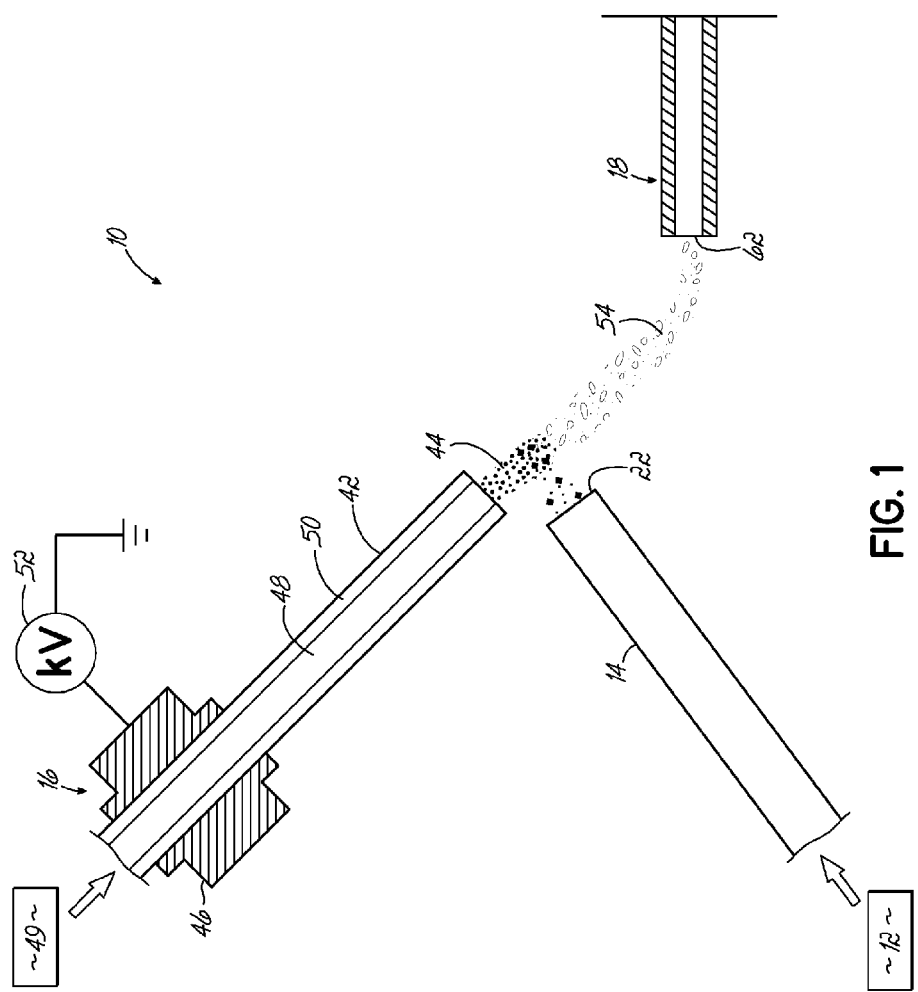
FIG. 1 is a diagrammatic cross sectional view of an embodiment of the present invention.

Although the present invention can be used with any acidic compound that suffers ion suppression in the presence of other compounds by traditional ionization method, such as ESI, it is particularly useful in the analysis of phosphoproteins and sulfated proteins. For purpose of description, a target compound, such as phosphopeptides, is made very acidic by addition of an appropriate strong acid to prevent suppression of the phosphopeptide signal by non-phosphorylated peptides. However, in general, this method is applicable to acidic compounds.

When the present invention is used for analysis of phosphopeptides, the phosphopeptide is combined with a strong acid that does not interfere with subsequent analysis utilizing a mass spectrometer. The phosphopeptide combined with the acid is referred to as a pre-acidified sample. In particular, haloacids, such as hydrochloric acid and hydrobromic acid can be combined with the phosphopeptide to achieve a desired pH of approximately 0 to 2.0. The acids must have a pKa1 smaller than the pKa1 of phosphoric acid, which is 2.12. Further, the strong acid must not provide a counter ion that interferes with the detection of the group of the phosphopeptides. Therefore, acids such as sulfuric acid and phosphoric acid are unsuitable for use in the present invention.

Briefly, the present invention provides a method for phosphoprotein analysis using DESI-MS. An apparatus 10 suitable for practicing the present invention includes a conduit 14 for the pre-acidified sample 12, an ambient ionizer 16, and the mass spectrometer 18. The pre-acidified sample 12 comprises an acidic organic target compound. The pre-acidified sample 12 is delivered through conduit 14 having an outlet 22. The conduit 14 may comprise, for example, a fused silica transfer capillary having an inner diameter of approximately 0.05 mm to approximately 0.2 mm. More specifically, the capillary may have an inner diameter of approximately 100 µm. The pre-acidified sample 12 may flow through the conduit 14 at a rate of approximately 1 µL/min to approximately 5 µL/min.

The ambient ionizer 16 includes a spray probe 42, which generates microdroplets of a charged solvent 44 and directs the charged solvent 44 toward the pre-acidified sample 12 that emerges from the conduit outlet 22. The spray probe 42 may be positioned approximately 0.5 mm to approximately 5 mm from the conduit outlet 22, for example. More specifically, the spray probe 42 may be positioned approximately 1 mm from the conduit outlet 22. The charged solvent 44 ionizes the pre-acidified sample 12 that emerges from the conduit outlet 22.

As shown, the ambient ionizer 16 is a DESI apparatus that includes a housing 46 having a solvent conduit 48 for solvent 49 surrounded by a gas conduit 50. The solvent 49 that is supplied to the ambient ionizer 16 may comprise, for example, methanol/water (1:1 by volume) containing 1% acetic acid. A voltage generator 52 is attached to the housing 46 and is operable to charge the solvent 49 within the solvent conduit 48. A high voltage of approximately 4 kV to approximately 5.5 kV may be applied to the solvent 49. More specifically, a voltage of approximately 5 kV may be applied to the solvent 49. The DESI apparatus generates the nebulized, charged solvent 44 that ionizes the pre-acidified sample 12 by desorption, forming an ionized sample 54. The DESI solvent flow rate may be from about 0.05 µL/min to approximately 50 µL/min. More specifically, the solvent 49 may be injected into the DESI apparatus at a rate of approximately 10 µL/min.

An LS-DESI-MS system is described in further detail in U.S. Pat. Nos. 7,915,579 and 8,330,119, the disclosures of which are incorporated in their entireties herein by reference.

The spray impact of the microdroplets of charged solvent 44 from the spray probe 42 with the pre-acidified sample 12 ionizes and deflects an ionized portion of the sample 54 into a mass spectrometer 18, such as a Thermo Finnigan LCQ DECA ion trap mass spectrometer 18 (Thermo Scientific, San Jose, Calif.). The mass spectrometer 18 has a sample entrance or opening 62, such as a heated capillary, which is also positioned near the conduit outlet 22 and the spray probe 42 of the ambient ionizer 16. The opening 62 may be positioned approximately 10 mm from the conduit outlet 22. The ionized sample 54 enters the opening 62, where a pump (not shown) maintains the atmosphere in the mass spectrometer 18 as a vacuum. The mass spectrometer 18 analyzes a mass-to-charge ratio of the ionized sample 54, as described in U.S. Pat. Nos. 7,915,579 and 8,330,119. In this way, the mass spectrometer 18 is configured to identify and quantify an amount of the target compound.

In use, a pre-acidified sample 12 of, for example, acidified phosphopeptide solution that has been acidified by a strong acid, such as HCl, is provided. The introduction of the strong acid lowers the pH of the phosphopeptide solution and suppresses the deprotonation of peptide phosphate groups in the solution. The pre-acidified sample 12 is delivered through conduit 14 and emerges through a conduit outlet 22, which is positioned proximate a spray probe 42 of the ambient ionizer 16. Solvent 49 is directed through an ambient ionizer 16, such as a DESI ionizer, which contacts the pre-acidified sample 12 and ionizes the pre-acidified sample 12 emerging from the conduit outlet 22. The ionization deflects an ionized portion of the sample 54 into an opening 62 of a mass spectrometer 18. The mass spectrometer 18 analyzes a mass-to-charge ratio of the ionized sample 54. In this way, the mass spectrometer 18 can identify and quantify an amount of the phosphopeptide target compound.

The method of the present invention helps prevent suppression of phosphopeptide signals during phosphoprotein analysis by MS. The intrinsic cause for the suppression of phosphopeptide ionization is that the phosphate groups of phosphopeptides tend to lose protons to carry negative charges. By adding a stronger acid than phosphoric acid to the target compound, phosphate deprotonation can be inhibited. Because the strong acid is added to the target compound prior to ionization, regular DESI-like solvent may be used for ionization.

As such, when the pre-acidified sample 12 is impinged by DESI spray 44 during ionization, the pre-acidified sample 12 is diluted by the DESI spray solvent 49, which reduces or prevents corrosion of the instruments in the apparatus 10. With the strong acid additives in the pre-acidified sample 12, phosphopeptides are charged as positive ions in the pre-acidified sample 12, which enables the pre-acidified sample 12 to be quickly converted from liquid phase to gas phase by DESI. Indeed, a 100% coverage of phosphorylated peptides is enabled by DESI-MS using only a few pmol of proteins. In addition, increased charges of phosphopeptide ions are also noted, which is valuable for tandem MS analysis.

This DESI-MS methodology may also be used for analysis of other acidic biomolecules, such as a sialic acid, a sialylated glycan, a phosphorylated protein, a sulphated protein or peptide, or a nucleic acid.

The present invention will be further appreciated in light of the following examples.

Experiment 1

Figure 2A:
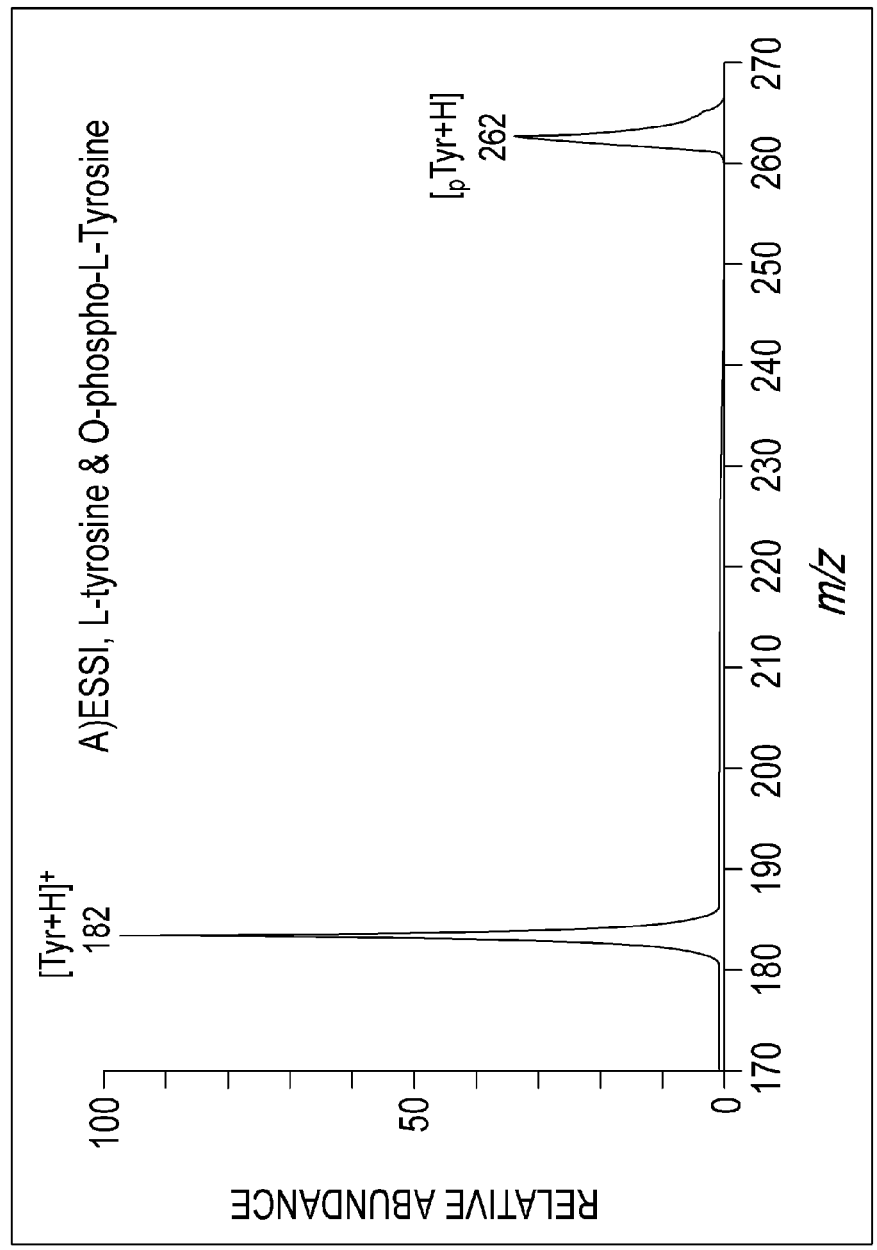
FIG. 2A is an ESSI-MS spectrum according to Experiment 1.
Figure 2B:
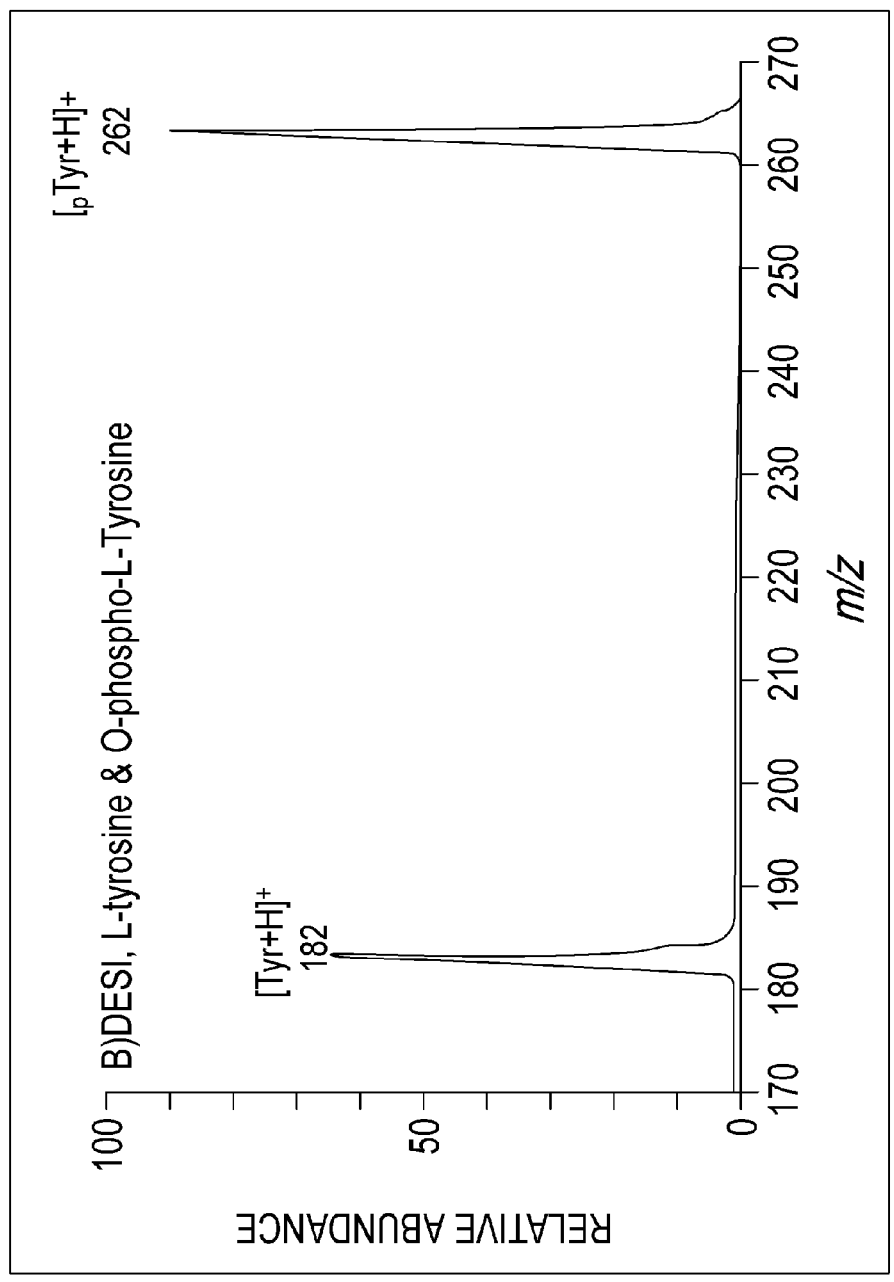
FIG. 2B is a DESI-MS spectrum according to Experiment 1.

With reference to FIGS. 2A-2B, O-phospho-L-tyrosine, a phosphorylated amino acid, was chosen as a test sample for a proof-of-principle experiment. When an amino acid mixture containing O-phospho-L-tyrosine and L-tyrosine (molar ratio 3:1) in MeOH/H$_2$O/HOAc (pH=3.3) was ionized by electronsonic spray ionization (ESSI, a variant form of ESI), the corresponding protonated molecules were observed at m/z 262 and 182, respectively (FIG. 2A). However, the intensity ratio of m/z 262 vs. m/z 182 is 0.3 although O-phospho-L-tyrosine is 3 times more concentrated than L-tyrosine, which shows the suppression of the phospho-amino acid in comparison to non-phosphorylated amino acids. Interestingly, when the amino acid mixture was acidified with HCl to pH 2.0 and ionized by DESI with the spray solvent 49 of MeOH/H$_2$O/HOAc, the signal intensity of m/z 262 exceeded m/z 182 (FIG. 2B). In addition, the absolute intensity of m/z, 262 in DESI-MS spectrum (2.0E7, arbitrary units, FIG. 2B) was higher than that in ESSI-MS spectrum (4.9E6, FIG. 2A). Evidently, the addition of HCl suppresses the deprotonation of phosphate group of O-phospho-L-tyrosine so that it can be more easily ionized by DESI.

Experiment 2

With reference to FIGS. 3A-4B, phosphoprotein digests were also examined with this DESI approach. α-Casein (sequence shown in FIG. 3A; the subscript "p" indicates that the residue serine is phosphorylated), a phosphoprotein carrying eight phosphate groups, was digested using trypsin following the reported procedure. In a comparison experiment using ESSI, among 16 peptide ions identified based on acquired MS spectrum (FIG. 3B; the figure inset shows the list of identified peptide ions), three phosphopeptide ions [VPQLEIVPN$_p$SAEER+2H]$^{2+}$ (SEQ. ID. NO. 1) (m/z 832), [YKVPQLEIVPN$_p$SAEER+2H]$^{2+}$ (SEQ. ID. NO. 2) (m/z 977), and [YKVPQLEIVPN$_p$SAEER+H]$^+$ (SEQ. ID. NO. 2) (m/z 1953) were detected, covering only one phosphorylation site of the protein. Other phosphorylated peptides are missing in the spectrum, emphasizing the well-known ion suppression effect mentioned above. In a stark contrast, when the sample was acidified by HCl to pH 2.0 and analyzed by DESI, besides the 16 peptide ions seen in the ESSI-MS spectrum, two additional doubly charged ions, [DIG$_p$SE$_p$STEDQAMEDIK+2H]$^{2+}$ (SEQ. ID. NO. 3) (m/z 965) and [QMEAE$_p$SI$_p$S$_p$S$_p$SEEIVPN$_p$SVEQK+2H]$^{2+}$ (SEQ. ID. NO. 4) (m/z 1361), were detected (FIG. 3C). The successful visualization of the highly acidic phosphopeptide QMEAE$_p$SI$_p$S$_p$S$_p$SEEIVPN$_p$SVEQK (SEQ. ID. NO. 4) is remarkable as it carries 5 phosphates. Upon collision-induced dissociation (CID), m/z 965 gives rise to fragment ions y$_4$, y$_5$, y$_6$, y$_8$ along with losses of one and two molecules of H$_3$PO$_4$ (FIG. 4A), and m/z 1361 dissociates into b$_5$, b$_7$, b$_{13}$, b$_{14}$, y$_5$, y$_7$, y$_8$, y$_9$, y$_{10}$, y$_{14}$ along with loss of one H$_3$PO$_4$ molecule (FIG. 4B), confirming their structures. The detection of these two additional phosphopeptides, DIG$_p$SE$_p$STEDQAMEDIK (SEQ. ID. NO. 3) and QMEAE$_p$SI$_p$S$_p$S$_p$SEEIVPN$_p$SVEQK (SEQ. ID. NO. 4), allows to cover all eight phosphorylation sites of the protein. In this experiment, only 5 pmol of α-casein digest was injected for ionization to acquire the DESI-MS spectrum, suggesting the high sensitivity of the method.

Figure 3B:
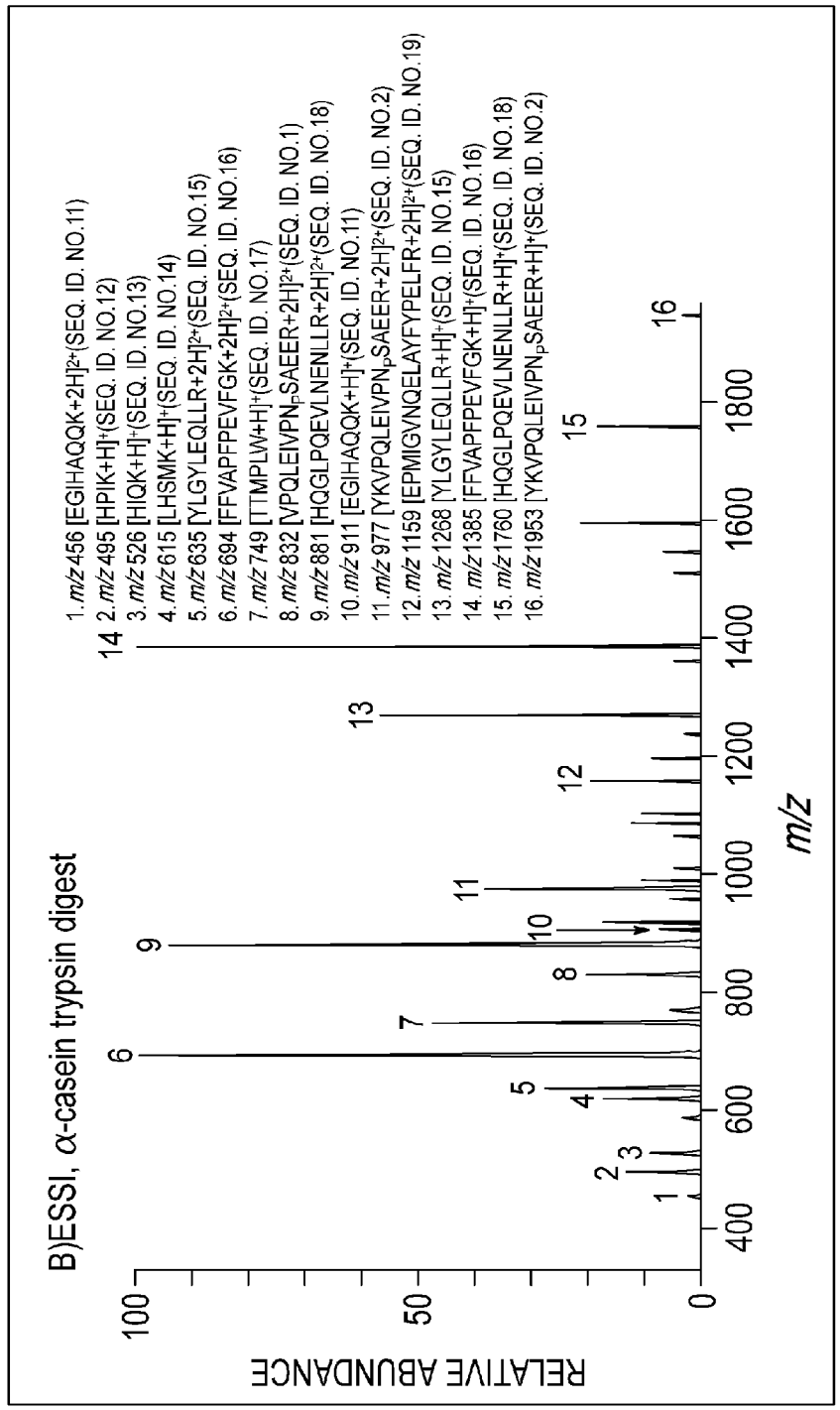
Figure 3C:
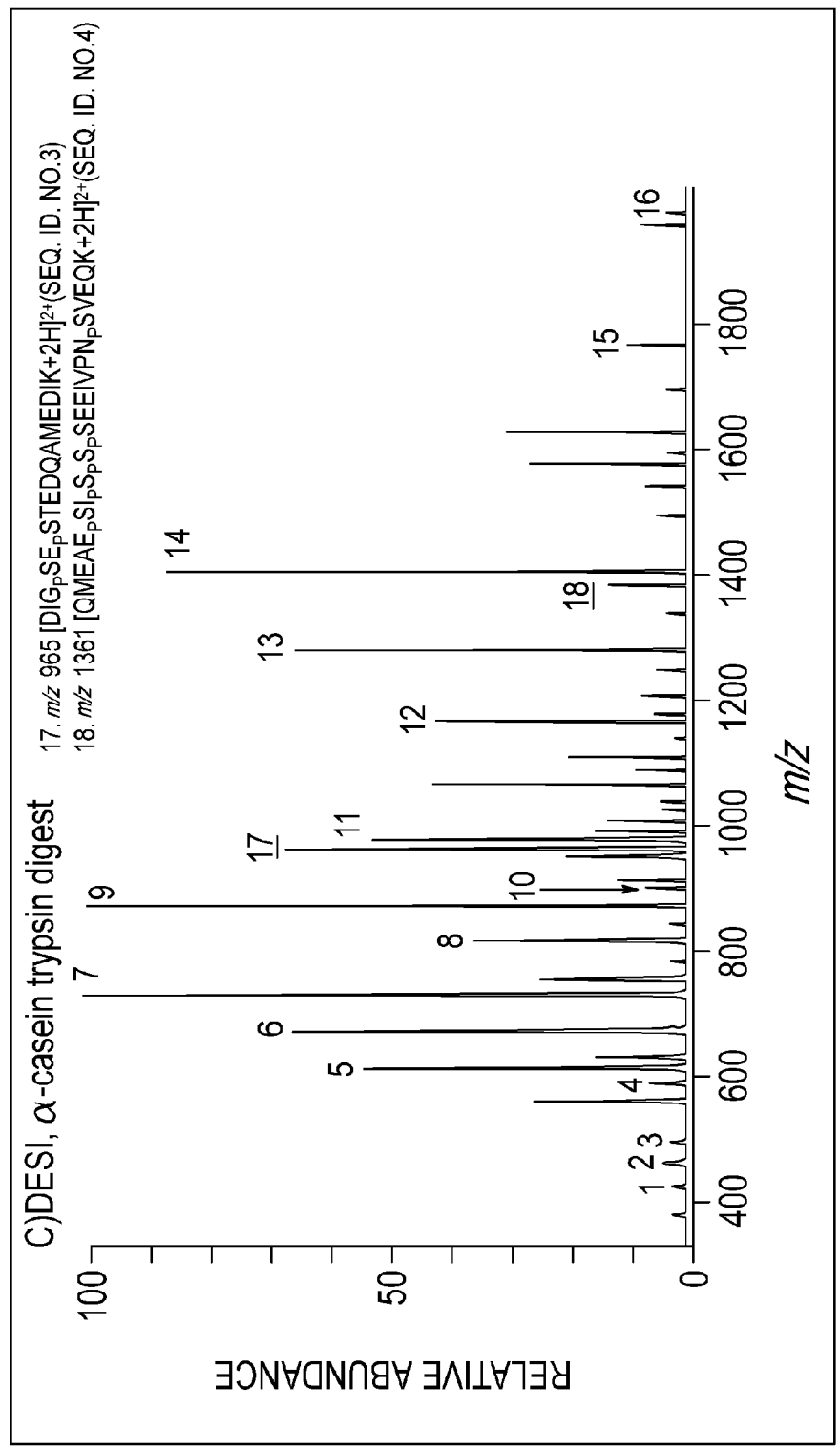
Figure 3D:
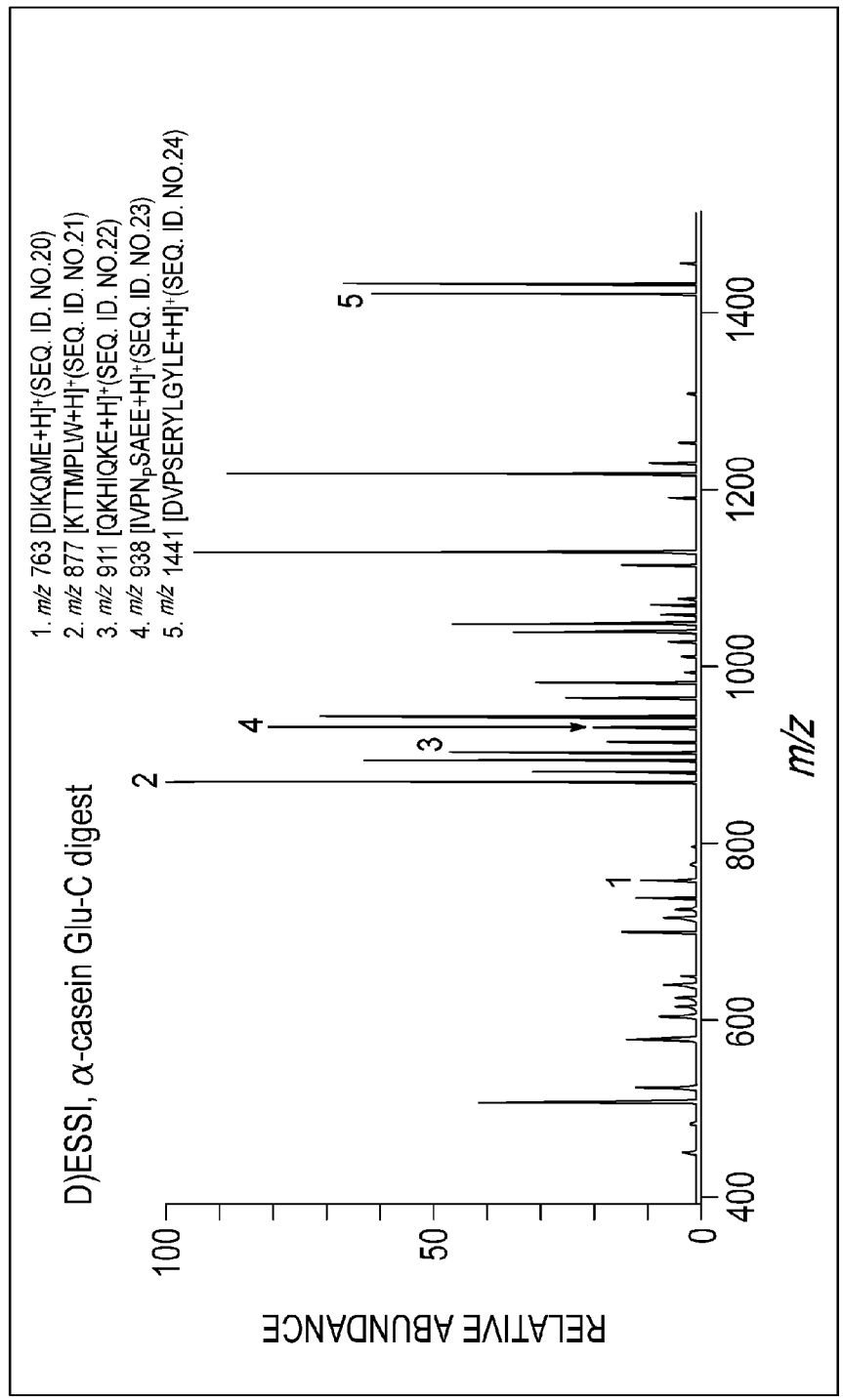
Figure 4A:
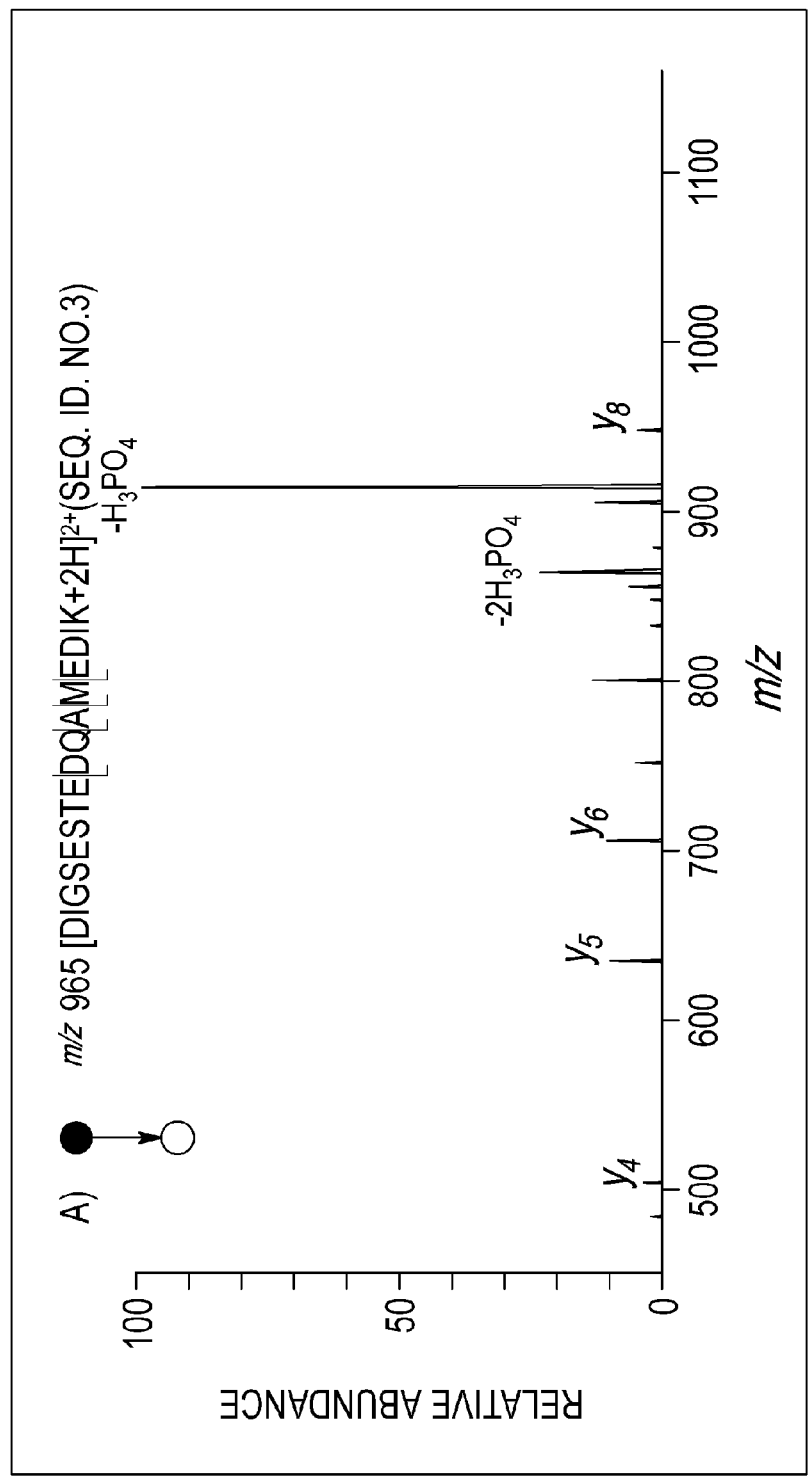
FIGS. 4A-4B are CID MS/MS spectra according to Experiment 2.
Figure 4B:
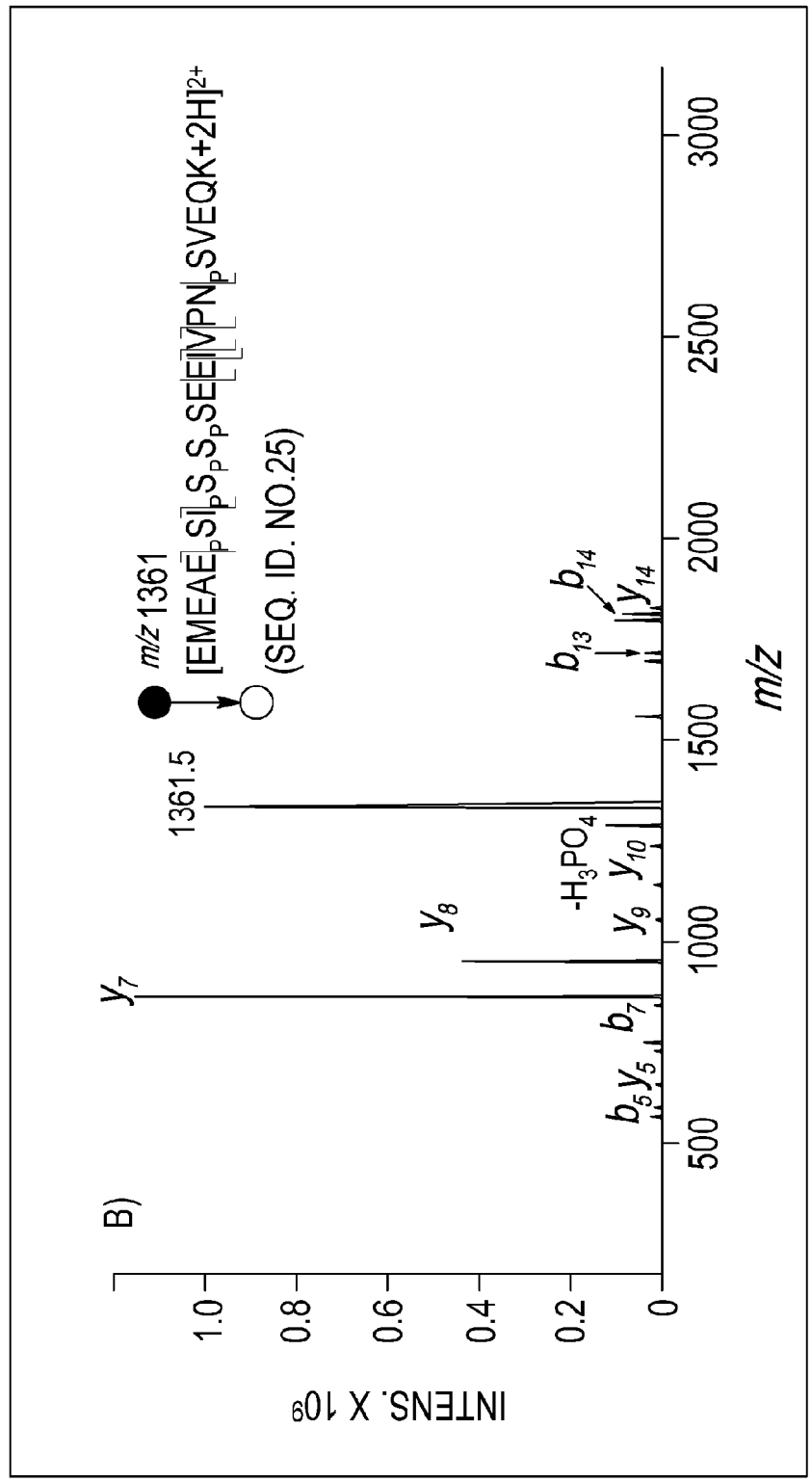

The feasibility of this DESI method was further confirmed with another sample, the α-casein Glu-C digest. Unlike trypsin digestion producing peptides carry a basic residue at the C-terminal, Glu-C selectively cleaves peptide bonds C-terminal to glutamic acid residues, which may provide phosphopeptides without any basic residues that would be more sensitive to the signal suppression effect. Indeed, only one phosphopeptide ion [IVPN$_p$SAEE+H]$^+$ (SEQ. ID. NO. 23) (m/z 938) appears in the ESSI-MS spectrum (FIG. 3D). After acidification with HCl and being ionized by DESI, two more phosphopeptide ions, [LSKDIG$_p$SE$_p$STE+H]$^+$ (SEQ. ID. NO. 6) (m/z 1326) and [AE$_p$SI$_p$S$_p$S$_p$SEEIVPN$_p$SVE+2H]$^{2+}$ (SEQ. ID. NO. 7) (m/z 1039) were detected (FIG. 3E), again covering all phosphate-carrying residues in the protein.

Experiment 3

The corrosion effect of HCl used in DESI to the mass spectrometer 18 instrument was evaluated in a separate experiment. A piece of stainless steel (316 S.S) was chosen to block the opening 62 of the mass spectrometer 18 to receive the sprayed liquids from DESI. When a sample of MeOH/H$_2$O with pH adjusted to 2.0 by HCl was injected to undergo DESI ionization for 30 min (both the flow rates and the DESI spray solvent were kept the same as in the analysis of phosphopeptide samples), no detectable damage was noted. While the same sample (pH 2.0) was sprayed by ESSI for 30 min, some traces of black marks on the stainless steel surface were seen, indicating the occurrence of some corrosion. This result shows the strength of DESI in analyzing low pH samples. Sulfuric acid (H$_2$SO$_4$), another strong acid, was chosen to replace HCl for the DESI experiments; however, the ionization of the phosphopeptides failed, probably because SO$_4^{2-}$ anions form adducts with positively charged peptide ions. HCl, a volatile acid, appears to be a better choice for such a DESI experiment. Recently HCl was also reported to be employed as an additive to the counter-flow gas in ESI to change the charge numbers of resulting protein ions.

Experiment 4

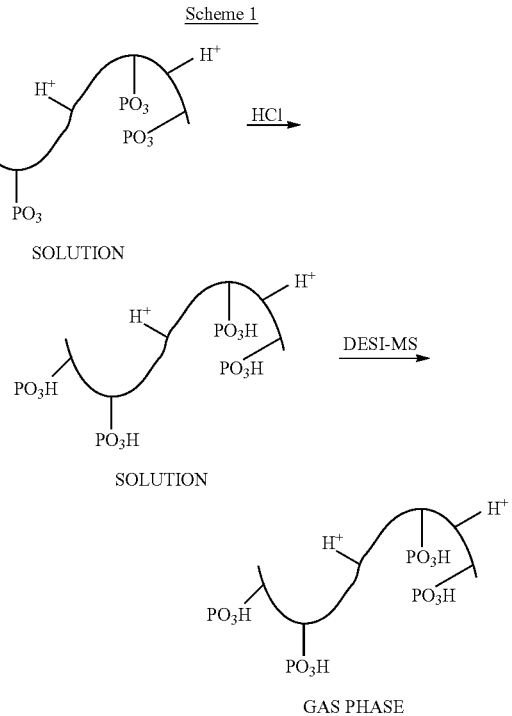

Scheme 1

Figure 5:
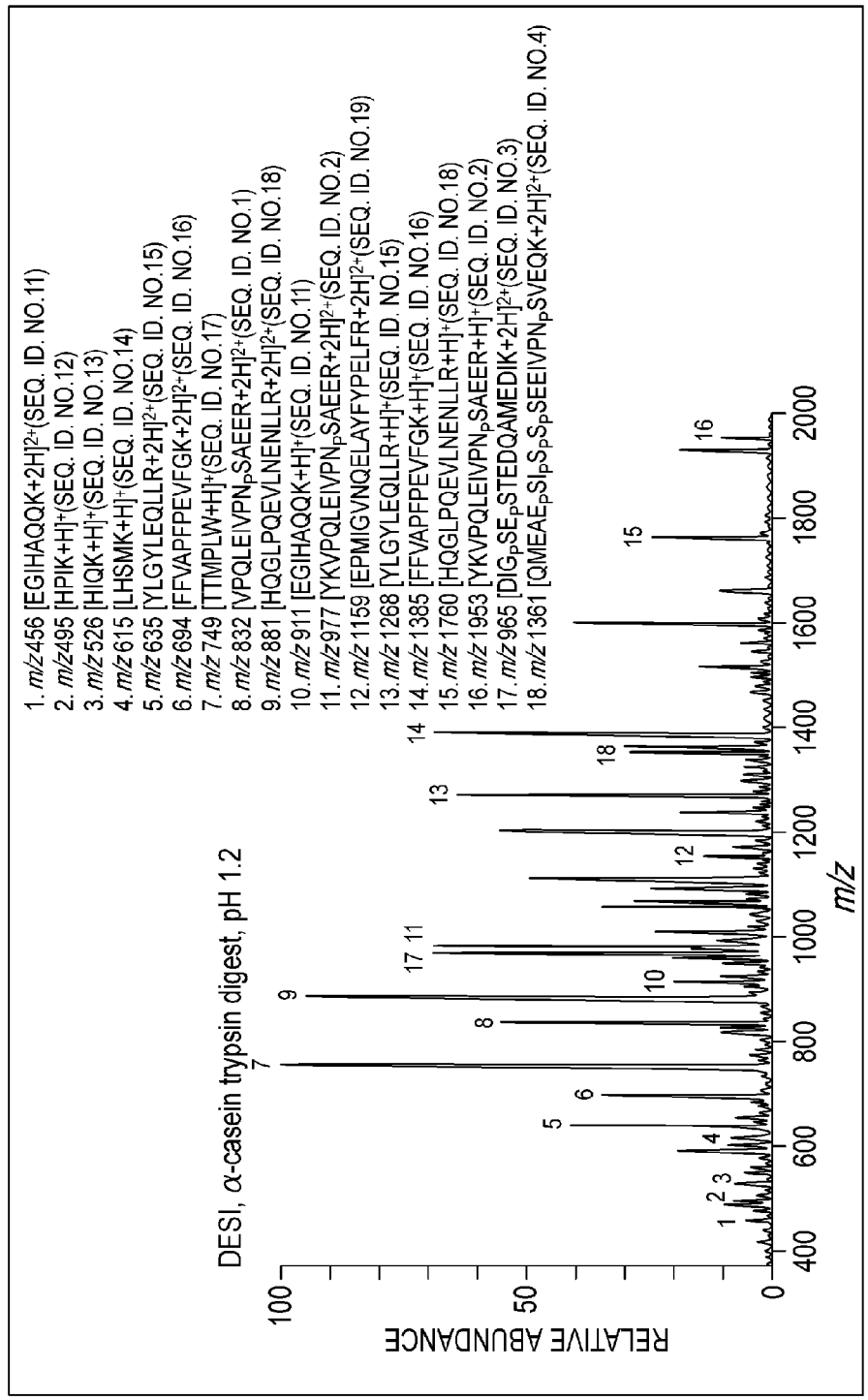
FIG. 5 is a DESI-MS spectrum according to Experiment 4.

A proposed mechanism for the efficient ionization of phosphopeptides from protein digests by DESI is depicted in Scheme 1. In a sample solution acidified with weak acids like acetic acid, phosphate groups carry negative charges due to deprotonation, which makes the phosphopeptides to be negatively charged. Once acidified with HCl to a low pH that suppresses the phosphate deprotonation, the phosphopeptides are positively charged in solution and therefore are able to compete with non-phosphorylated peptides to produce abundant positive ions by DESI. According to the Henderson-Hasselbalch equation pH=p$K_{a1}$+log([A$^-$]/(HA]) (HA and A$^-$ represent an acid and its conjugated base, respectively), the population of HA species (e.g., the intact phosphate group of phosphopeptides) can be further increased if the pH is lowered. This accounts for the contrast between the ionization of phosphopeptides at different pHs. Indeed, when the α-casein tryptic digest was acidified by HCl to pH 1.2, the signal intensity for [QMEAE$_p$SI$_p$S$_p$S$_p$SEEIVPN$_p$SVEQK+2H]$^{2+}$ (SEQ. ID. NO. 4) (m/z 1361) was further enhanced to 1.8E4 (FIG. 5) in comparison to that obtained via ionization at pH 2.0 (1.1E4, FIG. 3C). In the experiment of the ionization of pH 1.2 sample by DESI, the sample injection rate was reduced to 2 μL/min to avoid instrument corrosion. As shown in Scheme 1, these phosphopeptides positively charged in solution can be rapidly transferred into the gas phase by DESI for MS detection due to the direct sampling capability of DESI. An evidence to support this hypothesis is that, when the α-casein tryptic digest sample was mixed with the DESI spray solvent (1:2 by volume, mimicking the mixing in the DESI ionization process) and then was analyzed by ESSI, the m/z 1361 was not observed (data not shown). Presumably, the m/z 1361 detected in DESI-MS (FIG. 3E) survived the spray/sample solution mixing process in DESI because of the very short DESI ionization time scale (approximately 1-2 milliseconds) that favors the preservation of positively charged phosphopeptides during the ionization.

Experiment 5

Figure 6B:
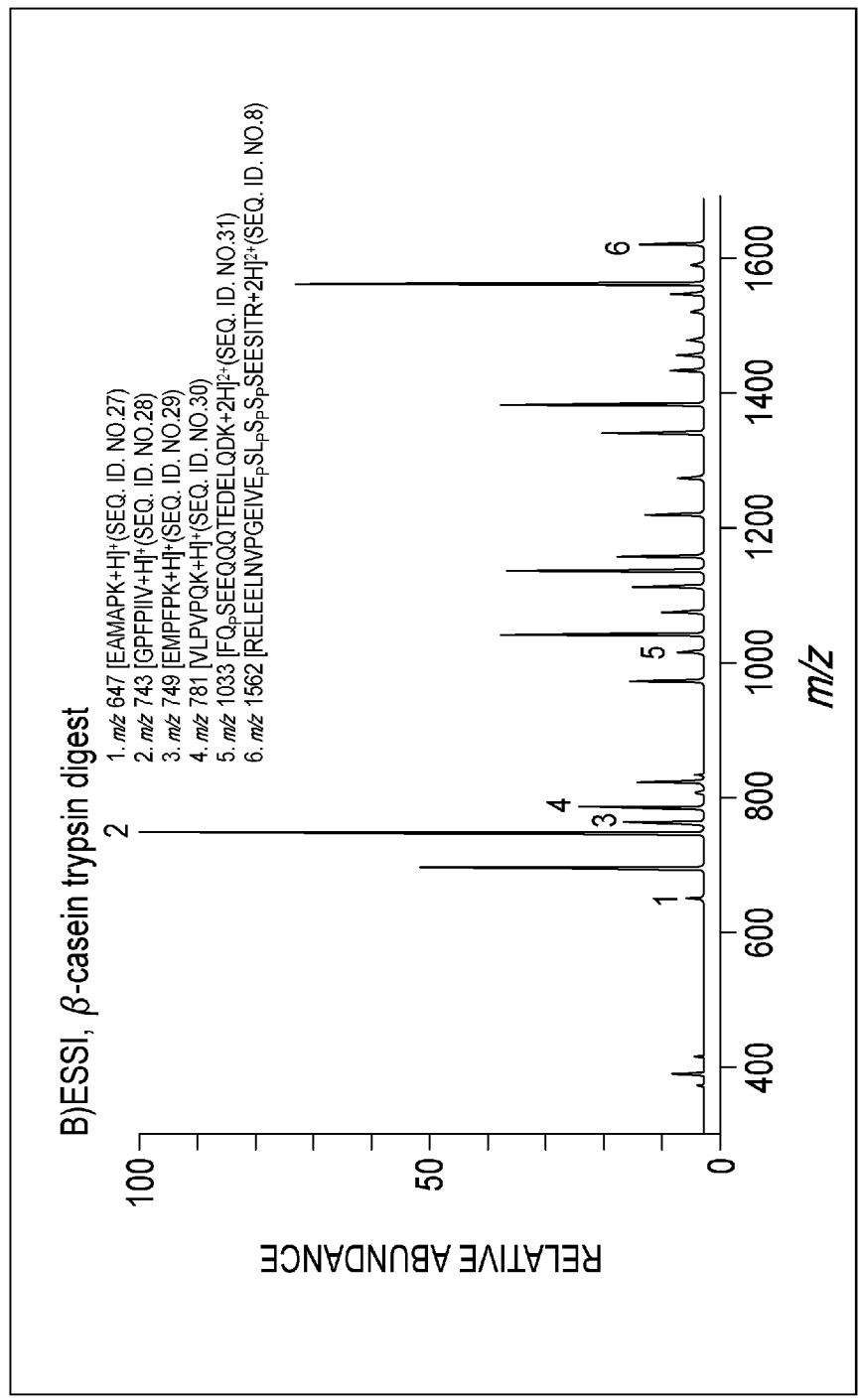
FIG. 6B is an ESSI-MS spectrum according to Experiment 5.
Figure 6C:
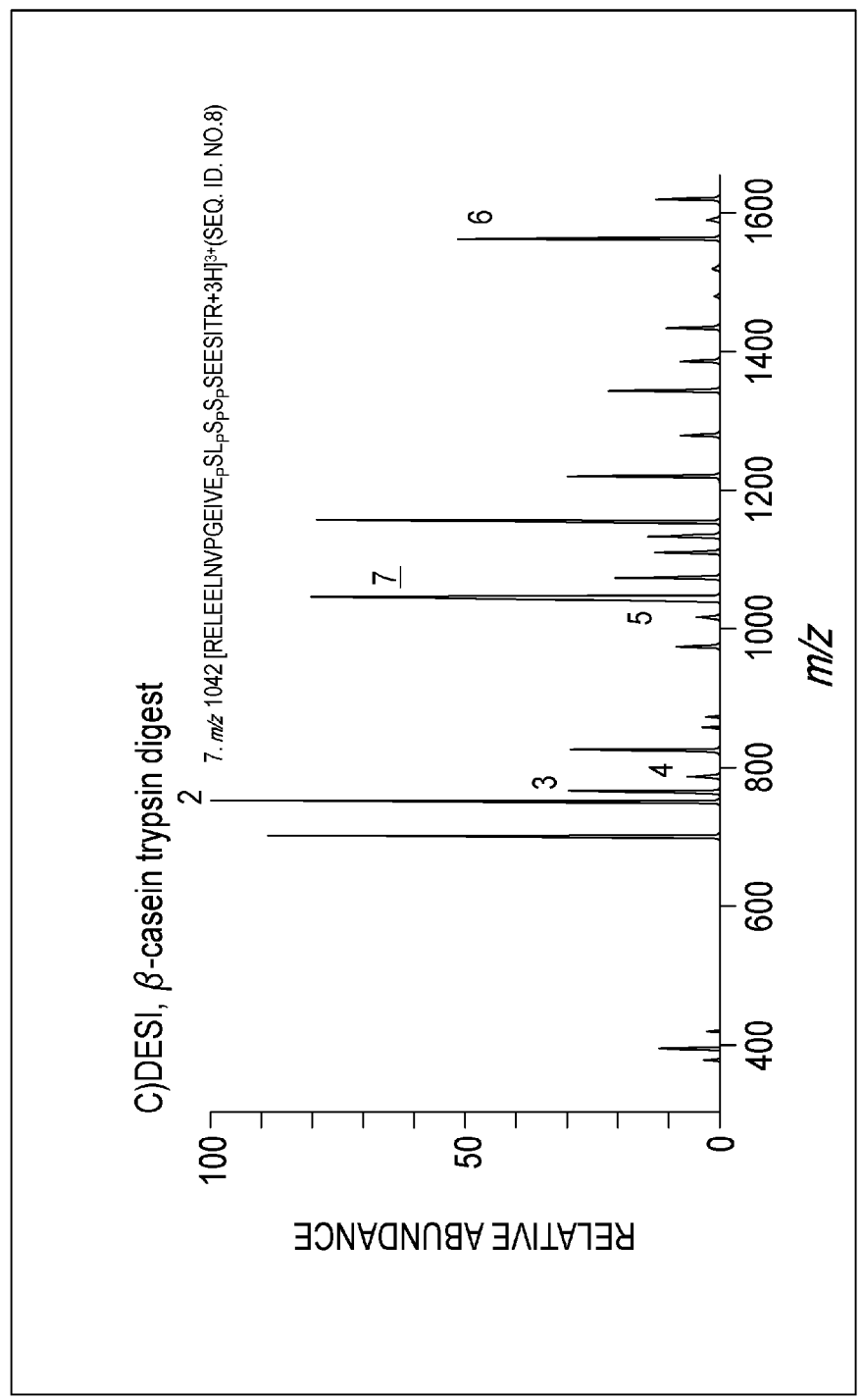
FIG. 6C is a DESI-MS spectrum according to Experiment 5.
Figure 7A:
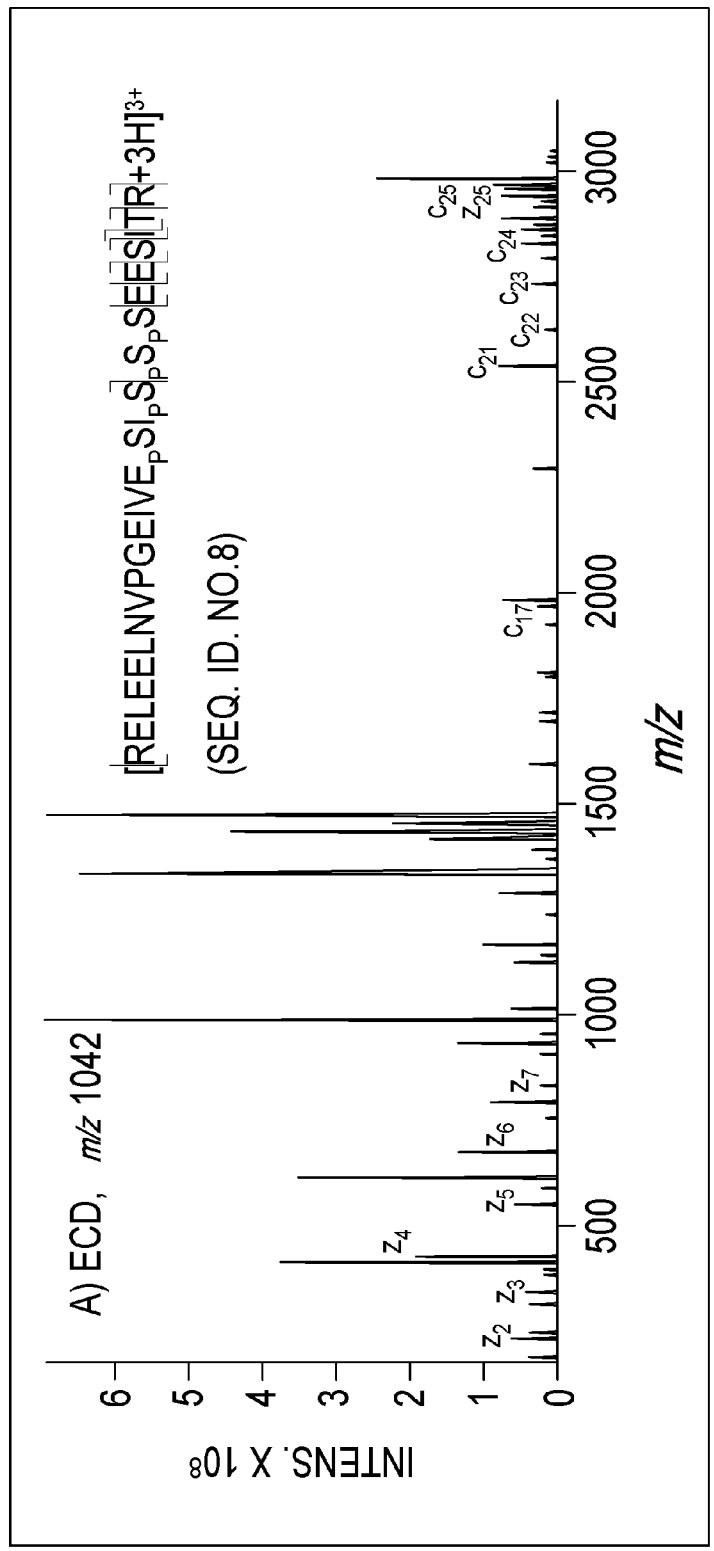
FIGS. 7A-7B are ECD MS/MS spectra according to Experiment 5.
Figure 7B:
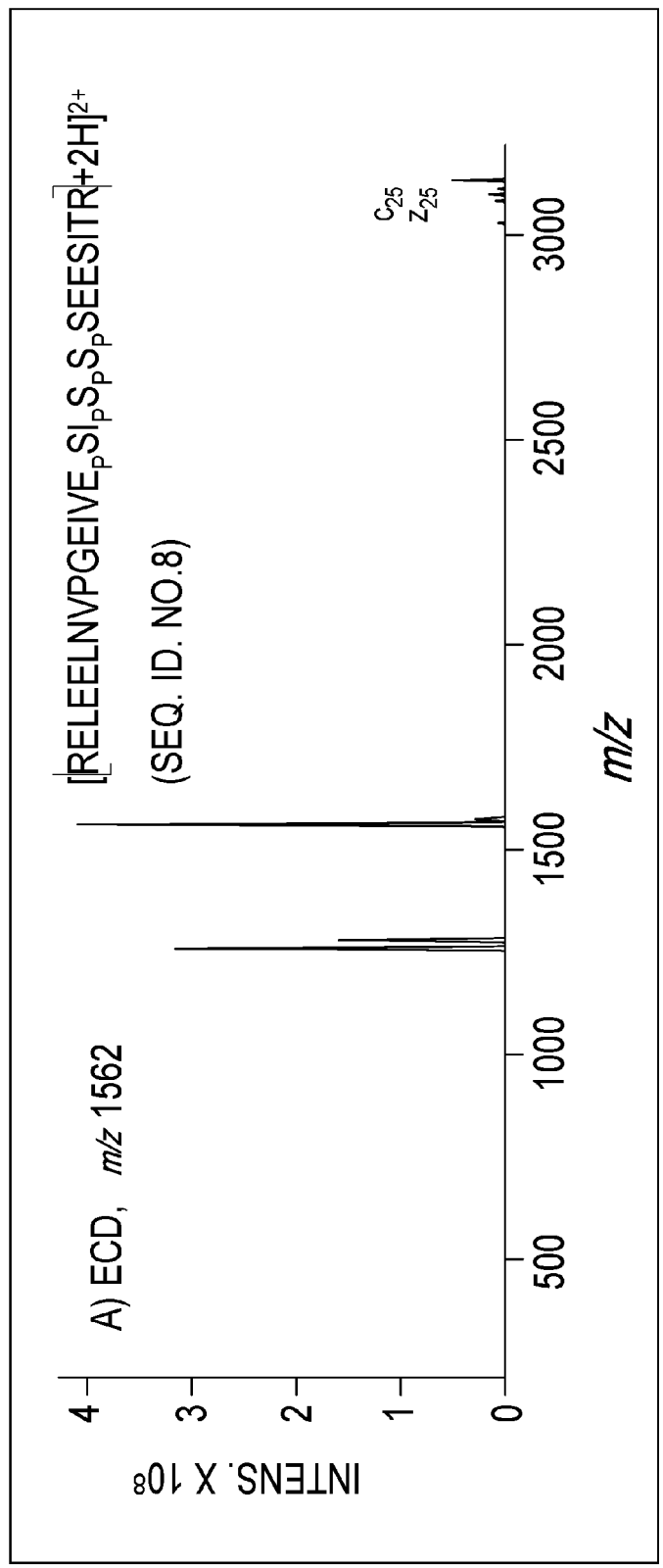

Besides the efficient ionization of highly acidic phosphopeptides from protein digests, charges of ionized phosphopeptides can also be enhanced using this DESI approach. For instance, in the case of β-casein tryptic digest (protein sequence shown in FIG. 6A), the intensity of the doubly charged ion [RELEELNVPGEIVE$_p$SL$_p$S$_p$S$_p$SEESITR+2H]$^{2+}$ (SEQ. ID. NO. 8) (m/z 1562) increased from 2.9E5 in ESSI-MS spectrum (FIG. 6B) to 5.1E5 in DESI-MS spectrum (FIG. 6C). More importantly, abundant triply charged ion [RELEELNVPGEIVE$_p$SL$_p$S$_p$S$_p$SEESITR+3H]$^{3+}$ (SEQ. ID. NO. 8) (m/z 1042) was generated (FIG. 6C). The enhanced charges would be valuable in providing increased sequence coverage via electron-based tandem MS analysis, such as electron-capture dissociation (ECD). Indeed, ECD of m/z 1042 gives rise to fragment ions of $z_2$, $z_3$, $z_4$, $z_5$, $z_6$, $z_7$, $c_{17}$, $c_{21}$, $c_{22}$, $c_{23}$, $c_{24}$, and $c_{25}$ (FIG. 7A) from which the locations of pSer[18] and pSer[19] of the protein can be clearly pinpointed. In contrast, ECD of m/z 1562 only gives rise to two fragment ions, $c_{25}$ and $z_{25}$ (FIG. 7B).

Figure 8A:
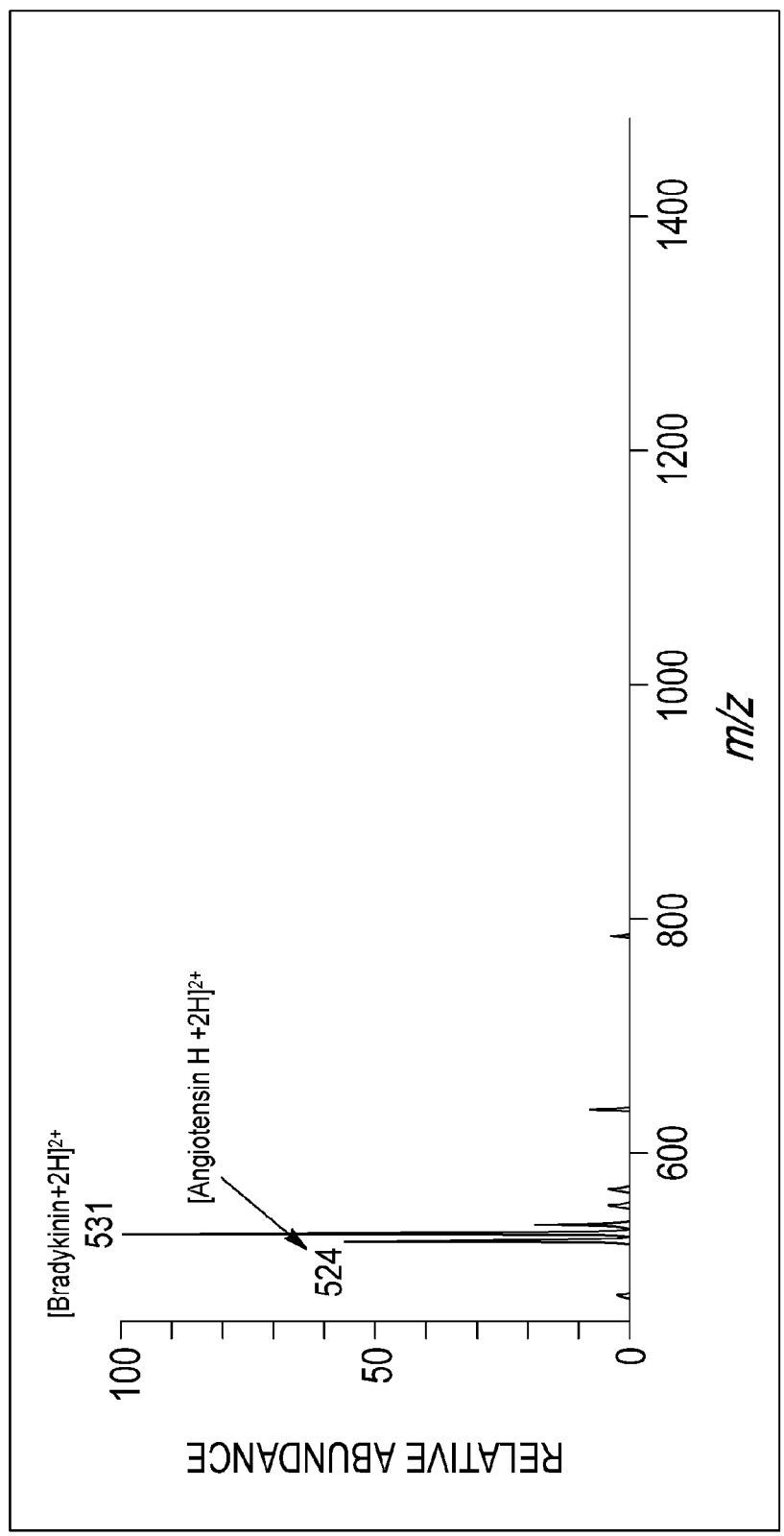
FIGS. 8A-8B are ESSI-MS spectrum according to Experiment 5.
Figure 8B:
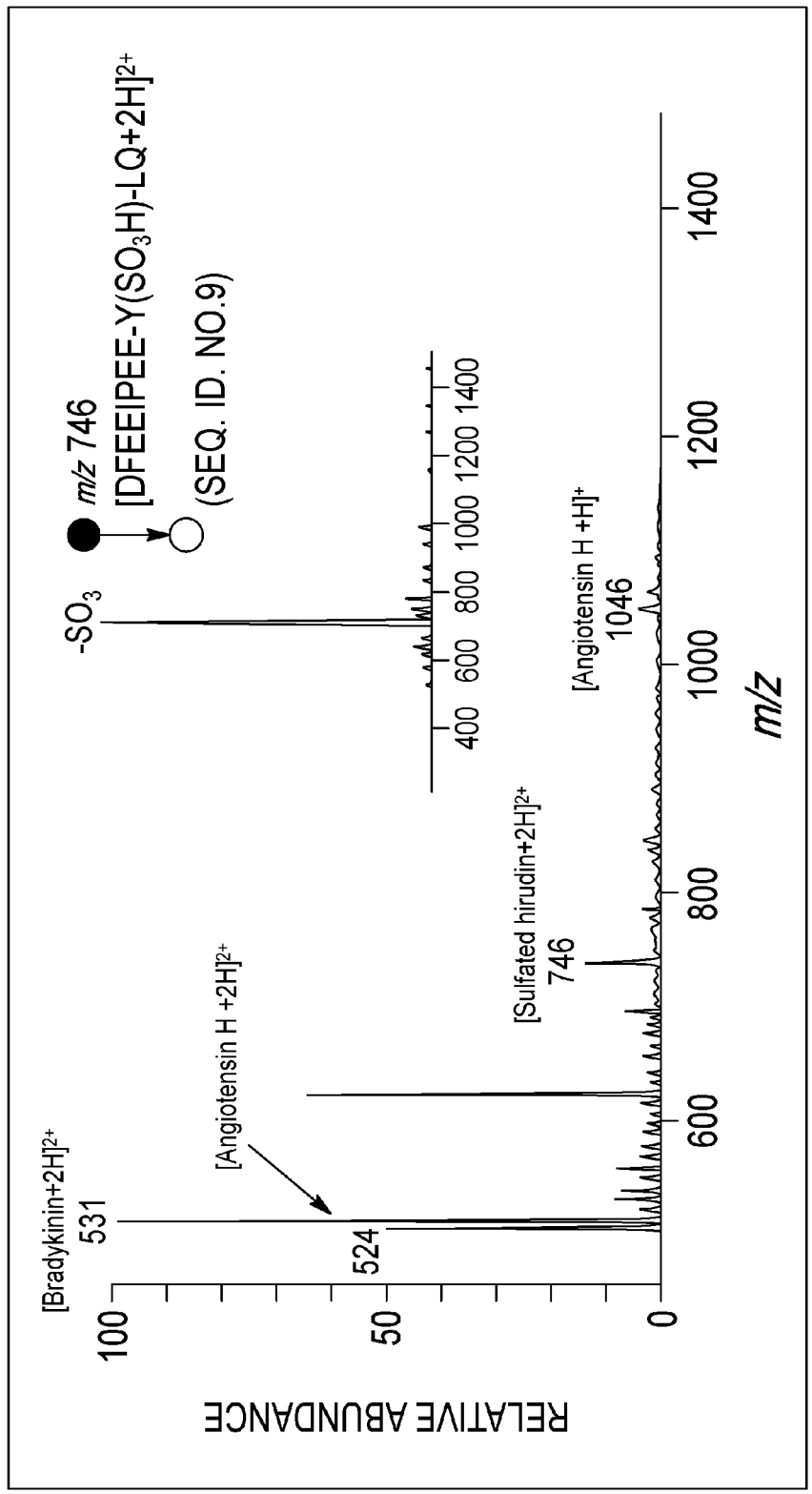

This DESI method is also applicable to the analysis of acidic sulfated peptides. Using a mixture containing sulfated hirudin (sequence: DFEEIPEE-Y(SO$_3$H)-LQ) (SEQ. ID. NO. 9), bradykinin and angiotensin II as a test sample (1:10:10 by moles), the sulfated hirudin was suppressed and no corresponding peptide ion was observed in ESSI-MS (FIG. 8A). In contrast, the doubly charged ions [DFEEIPEE-Y(SO$_3$H)-LQ+2H]$^{2+}$ (SEQ. ID. NO. 9) (m/z 746) arose via DESI-MS analysis (FIG. 8B), and its structure was confirmed by CID (the inset of FIG. 8B).

This invention presents a novel approach for solving the ion signal suppression problem that occurs with phosphopeptide ionization in protein digests by acidifying the target compound with strong acid HCl followed by direct DESI-MS analysis. The methodology is general, fast and sensitive. Efficient ionization can be achieved with the coverage of all phosphate carrying residues without laborious separation or enrichment of phosphopeptides. Thus, it reduces the cost of phosphoprotein analysis and saves time. The methodology of this invention is applicable for improving MS analysis of other important biomolecules with high acidity such as sialic acids, sialylated glycans, sulphated proteins, and nucleic acids.

This has been a description of the present invention along with the various methods of practicing the present invention. However, the invention itself should only be defined by the appended claims.

What is claimed is:

1. A mass spectrometry-based method for analyzing an acidic organic target compound having one or more phosphate groups, the method comprising:
   directing a charged solvent toward a pre-acidified sample having a pH of less than or equal to 2.0, the pre-acidified sample comprising the target compound and a strong acid, thereby ionizing the pre-acidified sample; and
   directing the ionized pre-acidified sample to a mass spectrometer, the mass spectrometer being configured to identify and quantify the target compound,
   wherein the strong acid is effective to suppress deprotonation of the one or more phosphate groups in the target compound.

2. The method of claim 1, wherein the pre-acidified sample comprises a blend of biomolecules.

3. The method of claim 2, wherein the biomolecules comprise a phosphopeptide.

4. The method of claim 2, wherein the biomolecules comprise one of a sialic acid, a sialylated glycan, a phosphorylated protein, a sulphated protein or peptide, and a nucleic acid.

5. The method of claim 1, wherein the strong acid comprises hydrochloric acid.

6. The method of claim 1, wherein the charged solvent is generated by desorption electrospray ionization.

7. The method of claim 1, wherein the charged solvent is generated by one of laser beam ionization, high energy particles ionization, plasma ionization, and ion beam ionization.

8. The method of claim 1, wherein the pre-acidified sample has a pH less than or equal to 1.2.

9. The method of claim 1, wherein the pre-acidified sample flows at a rate of 1 μL/min to 5 μL/min.

10. The method of claim 1, wherein ionization of the pre-acidified sample does not suppress ion signals in the pre-acidified sample.

11. The method of claim 1, further comprising:
   flowing the pre-acidified sample through a conduit, the conduit having an outlet positioned 0 mm from an opening of the mass spectrometer.

12. The method of claim 1, wherein the charged solvent is created by applying a voltage of 5 kV to a solvent.

13. A mass spectrometry-based method for effectively analyzing an acidic organic/biological compound in the presence of complicated matrix and for effectively removing/reducing the ion signal suppression effect, the method comprising:
   directing a charged solvent toward the pre-acidified sample comprising a target compound and a strong acid, the target compound comprising a phosphopeptide, thereby overcoming the ion suppression effect and ionizing the pre-acidified sample; and
   directing the ionized pre-acidified sample to a mass spectrometer, the mass spectrometer being configured to identify and quantify the target compound
   wherein the strong acid is effective to suppress deprotonation of phosphate groups in the phosphopeptide.

* * * * *

SEQUENCE LISTING

<160> NUMBER OF SEQ ID NOS: 31

<210> SEQ ID NO 1
<211> LENGTH: 14
<212> TYPE: PRT
<213> ORGANISM: Bos taurus

<400> SEQUENCE: 1

Val Pro Gln Leu Glu Ile Val Pro Asn Ser Ala Glu Glu Arg
1               5                   10

<210> SEQ ID NO 2
<211> LENGTH: 16
<212> TYPE: PRT
<213> ORGANISM: Bos taurus

<400> SEQUENCE: 2

Tyr Lys Val Pro Gln Leu Glu Ile Val Pro Asn Ser Ala Glu Glu Arg
1               5                   10                  15

<210> SEQ ID NO 3
<211> LENGTH: 16
<212> TYPE: PRT
<213> ORGANISM: Bos taurus

<400> SEQUENCE: 3

Asp Ile Gly Ser Glu Ser Thr Glu Asp Gln Ala Met Glu Asp Ile Lys
1               5                   10                  15

<210> SEQ ID NO 4
<211> LENGTH: 21
<212> TYPE: PRT
<213> ORGANISM: Bos taurus

<400> SEQUENCE: 4

Gln Met Glu Ala Glu Ser Ile Ser Ser Glu Glu Ile Val Pro Asn
1               5                   10                  15

Ser Val Glu Gln Lys
            20

<210> SEQ ID NO 5
<211> LENGTH: 8
<212> TYPE: PRT
<213> ORGANISM: Bos taurus

<400> SEQUENCE: 5

Ile Val Pro Asn Ser Ala Glu Glu
1               5

<210> SEQ ID NO 6
<211> LENGTH: 11
<212> TYPE: PRT
<213> ORGANISM: Bos taurus

<400> SEQUENCE: 6

Leu Ser Lys Asp Ile Gly Ser Glu Ser Thr Glu
1               5                   10

<210> SEQ ID NO 7
<211> LENGTH: 16
<212> TYPE: PRT
<213> ORGANISM: Bos taurus

<400> SEQUENCE: 7

Ala Glu Ser Ile Ser Ser Glu Glu Ile Val Pro Asn Ser Val Glu
1               5                   10                  15

<210> SEQ ID NO 8
<211> LENGTH: 25
<212> TYPE: PRT
<213> ORGANISM: Bos taurus

<400> SEQUENCE: 8

Arg Glu Leu Glu Glu Leu Asn Val Pro Gly Glu Ile Val Glu Ser Leu
1               5                   10                  15

Ser Ser Ser Glu Glu Ser Ile Thr Arg
            20                  25

<210> SEQ ID NO 9
<211> LENGTH: 11
<212> TYPE: PRT
<213> ORGANISM: Bos taurus

<400> SEQUENCE: 9

Asp Phe Glu Glu Ile Pro Glu Glu Tyr Leu Gln
1               5                   10

```
<210> SEQ ID NO 10
<211> LENGTH: 199
<212> TYPE: PRT
<213> ORGANISM: Bos taurus

<400> SEQUENCE: 10

Arg Pro Lys His Pro Ile Lys His Gln Gly Leu Pro Gln Glu Val Leu
1               5                   10                  15

Asn Glu Asn Leu Leu Arg Phe Phe Val Ala Pro Phe Pro Glu Val Phe
            20                  25                  30

Gly Lys Glu Lys Val Asn Glu Leu Ser Lys Asp Ile Gly Ser Glu Ser
        35                  40                  45

Thr Glu Asp Gln Ala Met Glu Asp Ile Lys Gln Met Glu Ala Glu Ser
    50                  55                  60

Ile Ser Ser Ser Glu Glu Ile Val Pro Asn Ser Val Glu Gln Lys His
65                  70                  75                  80

Ile Gln Lys Glu Asp Val Pro Ser Glu Arg Tyr Leu Gly Tyr Leu Glu
                85                  90                  95

Gln Leu Leu Arg Leu Lys Lys Tyr Lys Val Pro Gln Leu Glu Ile Val
            100                 105                 110

Pro Asn Ser Ala Glu Glu Arg Leu His Ser Met Lys Glu Gly Ile His
        115                 120                 125

Ala Gln Gln Lys Glu Pro Met Gly Ile Val Asn Gln Glu Leu Ala Tyr
    130                 135                 140

Phe Tyr Pro Glu Leu Phe Arg Gln Phe Tyr Gln Leu Asp Ala Tyr Pro
145                 150                 155                 160

Ser Gly Ala Trp Tyr Tyr Val Pro Leu Gly Thr Gln Tyr Thr Asp Ala
                165                 170                 175

Pro Ser Phe Ser Asp Ile Pro Asn Pro Ile Gly Ser Glu Asn Ser Glu
            180                 185                 190

Lys Thr Thr Met Pro Leu Trp
        195

<210> SEQ ID NO 11
<211> LENGTH: 8
<212> TYPE: PRT
<213> ORGANISM: Bos taurus

<400> SEQUENCE: 11

Glu Gly Ile His Ala Gln Gln Lys
1               5

<210> SEQ ID NO 12
<211> LENGTH: 4
<212> TYPE: PRT
<213> ORGANISM: Bos taurus

<400> SEQUENCE: 12

His Pro Ile Lys
1

<210> SEQ ID NO 13
<211> LENGTH: 4
<212> TYPE: PRT
<213> ORGANISM: Bos taurus

<400> SEQUENCE: 13

His Ile Gln Lys
1
```

```
<210> SEQ ID NO 14
<211> LENGTH: 5
<212> TYPE: PRT
<213> ORGANISM: Bos taurus

<400> SEQUENCE: 14

Leu His Ser Met Lys
1               5

<210> SEQ ID NO 15
<211> LENGTH: 10
<212> TYPE: PRT
<213> ORGANISM: Bos taurus

<400> SEQUENCE: 15

Tyr Leu Gly Tyr Leu Glu Gln Leu Leu Arg
1               5                   10

<210> SEQ ID NO 16
<211> LENGTH: 12
<212> TYPE: PRT
<213> ORGANISM: Bos taurus

<400> SEQUENCE: 16

Phe Phe Val Ala Pro Phe Pro Glu Val Phe Gly Lys
1               5                   10

<210> SEQ ID NO 17
<211> LENGTH: 6
<212> TYPE: PRT
<213> ORGANISM: Bos taurus

<400> SEQUENCE: 17

Thr Thr Met Pro Leu Trp
1               5

<210> SEQ ID NO 18
<211> LENGTH: 15
<212> TYPE: PRT
<213> ORGANISM: Bos taurus

<400> SEQUENCE: 18

His Gln Gly Leu Pro Gln Glu Val Leu Asn Glu Asn Leu Leu Arg
1               5                   10                  15

<210> SEQ ID NO 19
<211> LENGTH: 19
<212> TYPE: PRT
<213> ORGANISM: Bos taurus

<400> SEQUENCE: 19

Glu Pro Met Ile Gly Val Asn Gln Glu Leu Ala Tyr Phe Tyr Pro Glu
1               5                   10                  15

Leu Phe Arg

<210> SEQ ID NO 20
<211> LENGTH: 6
<212> TYPE: PRT
<213> ORGANISM: Bos taurus

<400> SEQUENCE: 20

Asp Ile Lys Gln Met Glu
1               5
```

<210> SEQ ID NO 21
<211> LENGTH: 7
<212> TYPE: PRT
<213> ORGANISM: Bos taurus

<400> SEQUENCE: 21

Lys Thr Thr Met Pro Leu Trp
1               5

<210> SEQ ID NO 22
<211> LENGTH: 7
<212> TYPE: PRT
<213> ORGANISM: Bos taurus

<400> SEQUENCE: 22

Gln Lys His Ile Gln Lys Glu
1               5

<210> SEQ ID NO 23
<211> LENGTH: 8
<212> TYPE: PRT
<213> ORGANISM: Bos taurus

<400> SEQUENCE: 23

Ile Val Pro Asn Ser Ala Glu Glu
1               5

<210> SEQ ID NO 24
<211> LENGTH: 12
<212> TYPE: PRT
<213> ORGANISM: Bos taurus

<400> SEQUENCE: 24

Asp Val Pro Ser Glu Arg Tyr Leu Gly Tyr Leu Glu
1               5                   10

<210> SEQ ID NO 25
<211> LENGTH: 21
<212> TYPE: PRT
<213> ORGANISM: Bos taurus

<400> SEQUENCE: 25

Glu Met Glu Ala Glu Ser Ile Ser Ser Glu Glu Ile Val Pro Asn
1               5                   10                  15

Ser Val Glu Gln Lys
            20

<210> SEQ ID NO 26
<211> LENGTH: 209
<212> TYPE: PRT
<213> ORGANISM: Bos taurus

<400> SEQUENCE: 26

Arg Glu Leu Glu Glu Leu Asn Val Pro Gly Glu Ile Val Glu Ser Leu
1               5                   10                  15

Ser Ser Ser Glu Glu Ser Ile Thr Arg Ile Asn Lys Lys Ile Glu Lys
            20                  25                  30

Phe Gln Ser Glu Glu Gln Gln Thr Glu Asp Glu Leu Gln Asp Lys
            35                  40                  45

Ile His Pro Phe Ala Gln Thr Gln Ser Leu Val Tyr Pro Phe Pro Gly
            50                  55                  60

Pro Ile Pro Asn Ser Leu Pro Gln Asn Ile Pro Pro Leu Thr Gln Thr

```
                65                  70                  75                  80
Pro Val Val Pro Pro Phe Leu Gln Pro Glu Val Met Gly Val Ser
                    85                  90                  95

Lys Val Lys Glu Ala Met Ala Pro Lys His Lys Glu Met Pro Phe Pro
                100                 105                 110

Lys Val Pro Val Glu Pro Phe Thr Glu Ser Gln Ser Leu Thr Leu Thr
                115                 120                 125

Asp Val Glu Asn Leu His Leu Pro Leu Pro Leu Leu Gln Ser Trp Met
            130                 135                 140

His Gln Pro His Gln Pro Leu Pro Pro Thr Val Met Phe Pro Pro Gln
145                 150                 155                 160

Ser Val Leu Ser Leu Ser Gln Ser Lys Val Leu Pro Val Pro Gln Lys
                165                 170                 175

Ala Val Pro Tyr Pro Gln Arg Asp Met Pro Ile Gln Ala Phe Leu Leu
                180                 185                 190

Tyr Gln Glu Pro Val Leu Gly Pro Val Arg Gly Pro Phe Pro Ile Ile
            195                 200                 205

Val

<210> SEQ ID NO 27
<211> LENGTH: 6
<212> TYPE: PRT
<213> ORGANISM: Bos taurus

<400> SEQUENCE: 27

Glu Ala Met Ala Pro Lys
1               5

<210> SEQ ID NO 28
<211> LENGTH: 7
<212> TYPE: PRT
<213> ORGANISM: Bos taurus

<400> SEQUENCE: 28

Gly Pro Phe Pro Ile Ile Val
1               5

<210> SEQ ID NO 29
<211> LENGTH: 6
<212> TYPE: PRT
<213> ORGANISM: Bos taurus

<400> SEQUENCE: 29

Glu Met Pro Phe Pro Lys
1               5

<210> SEQ ID NO 30
<211> LENGTH: 7
<212> TYPE: PRT
<213> ORGANISM: Bos taurus

<400> SEQUENCE: 30

Val Leu Pro Val Pro Gln Lys
1               5

<210> SEQ ID NO 31
<211> LENGTH: 16
```

```
<212> TYPE: PRT
<213> ORGANISM: Bos taurus

<400> SEQUENCE: 31

Phe Gln Ser Glu Glu Gln Gln Gln Thr Glu Asp Glu Leu Gln Asp Lys
1               5                   10                  15
```